United States Patent [19]

Raeder et al.

[11] 4,380,435
[45] Apr. 19, 1983

[54] PERMANENT ONE VISIT BONDED BRIDGE NO DRILLING, AND KIT THEREFOR

[76] Inventors: Arthur Raeder; Celia R. Raeder, both of 615 Eastern Pkwy., Brooklyn, N.Y. 11216

[21] Appl. No.: 209,321

[22] Filed: Nov. 24, 1980

Related U.S. Application Data

[63] Continuation-in-part of Ser. No. 938,423, Aug. 31, 1978, abandoned.

[51] Int. Cl.³ .............................................. A61C 13/22
[52] U.S. Cl. .................................... 433/180; 433/181; 433/183; 433/193; 433/217
[58] Field of Search ............... 433/180, 182, 190, 191, 433/192, 9, 215, 219, 177, 181, 183, 193, 217, 222, 223, 228

[56] References Cited

U.S. PATENT DOCUMENTS

| | | | |
|---|---|---|---|
| 374,572 | 12/1887 | Beale, Jr. | 433/191 |
| 1,449,079 | 3/1923 | Yirikian | 433/181 |
| 2,697,278 | 12/1954 | Kohler | 433/191 |
| 2,720,025 | 10/1955 | Miller | 433/191 |
| 3,216,111 | 11/1965 | Sink | 433/177 |
| 3,395,455 | 8/1968 | Overby et al. | 433/215 |
| 3,423,827 | 1/1969 | Bahn et al. | 433/183 |
| 3,429,043 | 2/1969 | Andrews | 433/183 |
| 3,487,545 | 1/1970 | Weissman | 433/215 |
| 3,641,670 | 2/1972 | Karageorge | 433/180 |
| 3,709,866 | 1/1973 | Waller | 260/42.52 |
| 3,822,472 | 7/1974 | Garfinkel | 433/219 |
| 3,986,261 | 10/1976 | Faunce | 433/217 |
| 3,987,545 | 10/1976 | Kennedy | 433/223 |
| 4,097,994 | 7/1978 | Reaville et al. | 433/217 |
| 4,259,117 | 3/1981 | Yamauchi et al. | 433/217 |
| 4,298,005 | 11/1981 | Mutzhas | 250/504 R |

FOREIGN PATENT DOCUMENTS 2557020  6/1977  Fed. Rep. of Germany ...... 433/229

*Primary Examiner*—Gene Mancene
*Assistant Examiner*—Michael J. Foycik, Jr.
*Attorney, Agent, or Firm*—Ostrolenk, Faber, Gerb & Soffen

[57] ABSTRACT

A dental prosthesis and process of making and installing the same, wherein a plurality of individual artificial teeth are assembled on an arched contoured longitudinal support, are disclosed, as well as a kit containing detailed instructions and necessary supplies and equipment for carrying out the process. The artificial teeth are made of an acrylic resin, other composites or plastics or porcelain. Anterior natural teeth adjacent the space to be filled are step shaped lingually and etched to provide a base for bonding. Posterior teeth adjacent the space have the fossae deepened if needed. The arched contoured longitudinal support carrying the proper number of artificial teeth integrated with the support and each other is placed in the formed steps or deepened fossae on opposite sides of the space and bonded in place, lapped and smoothed. The procedure permits assembly of the prosthesis from separate teeth by the dentist and permits virtually all operations to be performed by the dentist—even on a one-visit basis. The margins of the prosthesis do not infringe on the crevicular space; therefore no irritating factors affect the gingival sulcus and no periodontal disease will result from the prosthesis. Flossing can be fully performed for hygiene purposes. This prosthesis performs all the functions of natural teeth including: mastication, speech, spatial support, facial contour and aesthetics.

29 Claims, 54 Drawing Figures

UPPER    LOWER

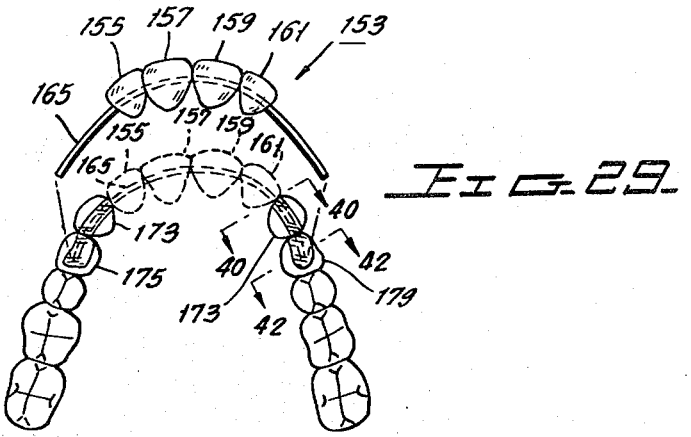
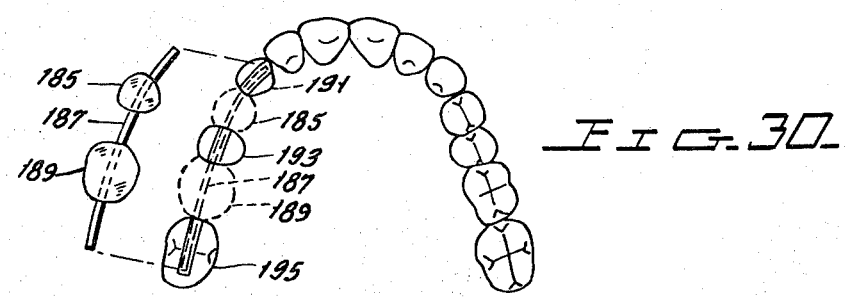
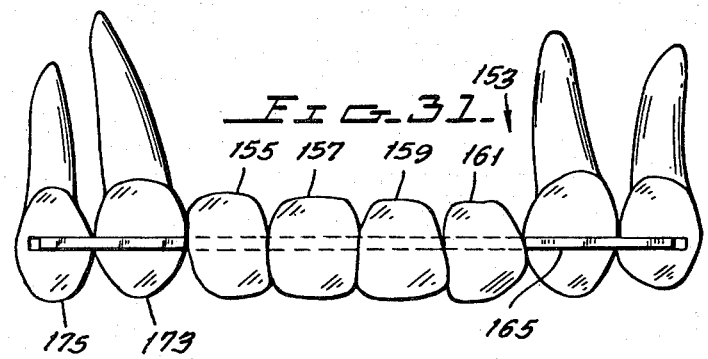
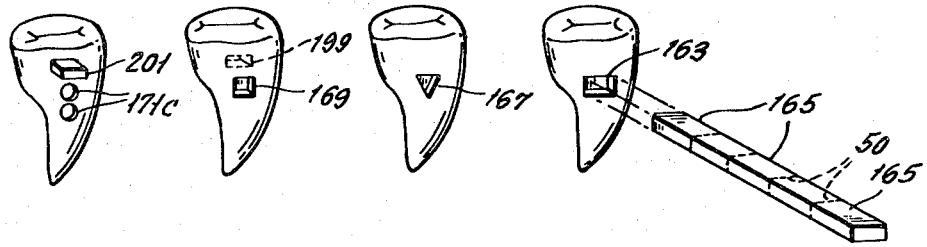

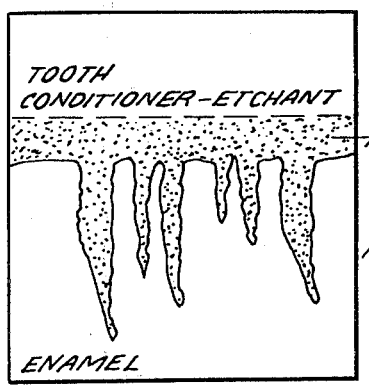
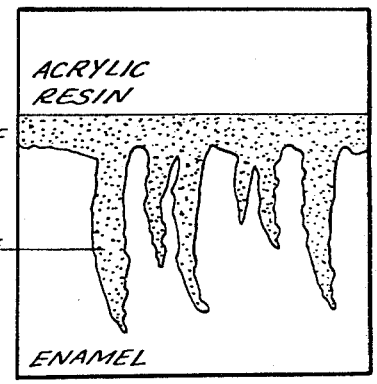
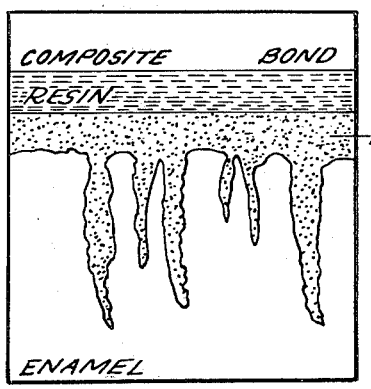
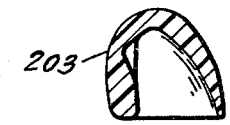
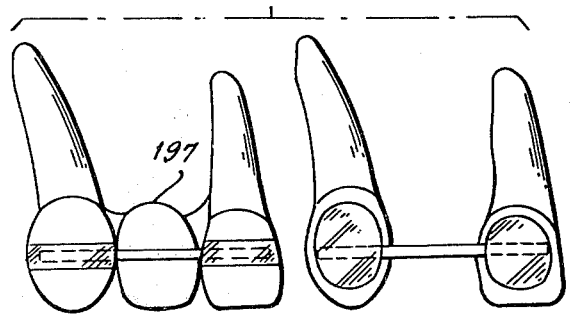
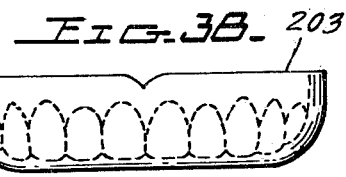
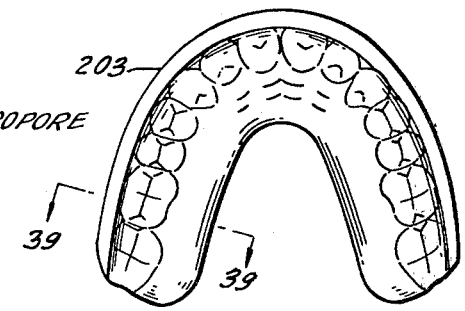

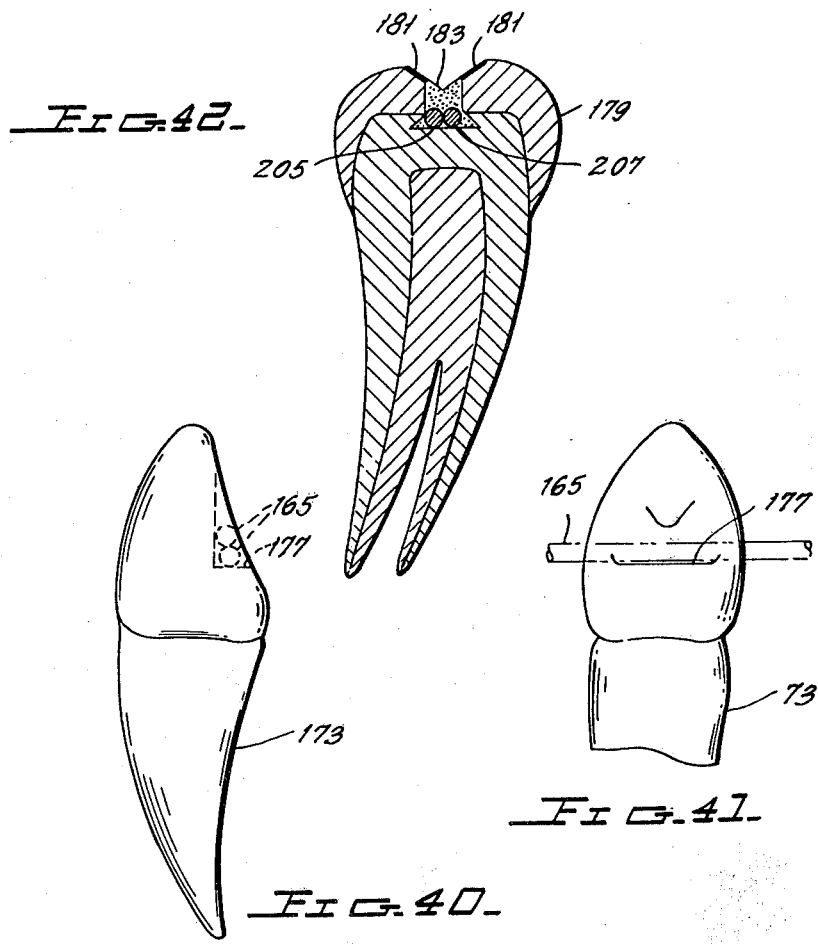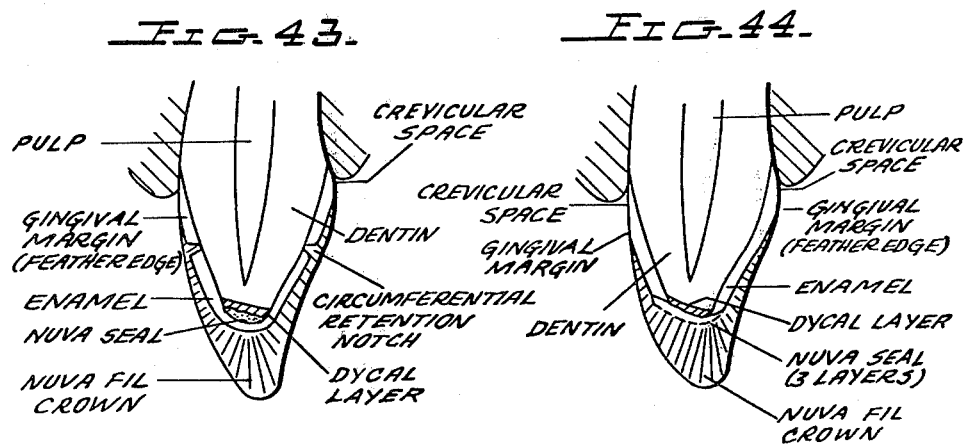

PERMANENT ONE VISIT BONDED BRIDGE NO DRILLING, AND KIT THEREFOR

This application is a continuation-in-part of application Ser. No. 938,423, filed Aug. 31, 1978 and now abandoned.

The present invention relates to dental prostheses and more particularly to a prosthesis which is permanently bonded to adjacent natural teeth, may be articulated precisely to the natural teeth, provides no interference with the natural teeth and is simple in construction, operation and insertion so that virtually no discomfort is created during the process.

The invention further relates to a kit containing the basic materials needed to make and install the prosthesis during a single visit of the patient. The kit includes detailed, fully illustrated instructions for carrying out the procedure described herein, as well as the elements necessary to perform the process.

This procedure does not necessitate placement of a temporary bridge between office visits which the traditional bridge construction requires because the bite collapses when the teeth are ground and not supported. The bite collapse which results may precipitate a temporomandibular joint problem which is known to have many deleterious results. Since minimum interference with the natural teeth is involved and the process is simplified to a substantial extent, the cost of the insertion of the permanent prosthesis is greatly reduced while the efficiency of the prosthesis (which may at times hereinafter be referred to as a bridge) is such that the action thereof with respect to the natural teeth so simulates the original tooth structure that the patient, after installation, will be completely comfortable and completely functional.

Heretofore in the creation of bridges or other prostheses where one or more artificial teeth are to be inserted in the mouth to be engaged with natural teeth, various methods have been used especially for permanent bridge work. One of the most frequently used methods is the grinding down of the two natural teeth on either side of the gap to mere stubs and the fitting of a prosthesis which consists of two crowns, one for each of the ground down natural teeth and the artificial teeth carried between the crowns; usually, the crowns and the artificial teeth are made as a single unit requiring an expensive series of steps and operations both by the dentist and the laboratory which may make the final structure which is to be inserted.

While it has been claimed that such interference with the natural teeth naturally results in strengthening them and that the cement holding the crown in place provides protection, the fact is that the natural teeth are mutilated and become mere stubs prior to the placement of the crowns thereon. The process is therefore irreversible. Should it be necessary to remove the bridge for any reason the natural teeth would still require the replacement of the crowns thereon whether or not the gap is left between the two natural teeth for any reason so that the natural teeth may continue to function as teeth and, of course, not interfere with the appearance of the individual or with the bite.

The present invention contemplates that, with respect to the front teeth, other than the biscuspid molars, a notch or rest be shaped on the lingual surface of the enamel of the anterior natural teeth in order to receive appropriate support for the artificial teeth. In the case of the biscupids and molars, the notch may be formed by deepening the central fossa of the occlusal surface of the enamel of the bicuspids and molars. Where a bridge is to span a space between a molar and, for instance, a cuspid, the notch may be formed in the central fossa of the molar and on the lingual surface of the cuspid. One or more internal metal longitudinal struts are then provided for the artificial teeth, and as many artificial teeth as are required for the particular bridge are placed on the strut being strung along the strut as needed and secured in place in any appropriate manner by any appropriate bond or other means. The artificial teeth may also be secured to each other as hereinafter pointed out.

One of the essential elements of the present invention, therefore, is not only minimum interference with the function, structure and appearance of the natural teeth but also the fact that the bridge may be assembled from a plurality of artificial teeth instead of being created as a single unit.

By this means, therefore, it is possible to provide a stock of artificial teeth which may be assembled for any particular bridge; and, while the bridge may be regarded as custom made to the particular individual or the particular order, the fact is that many steps which were previously required are avoided.

In making the kind of bridge which is presently used, after the adjacent natural teeth are ground down to stubs and appropriate impressions taken as hereinafter described, the bridge which is made usually consists of a pair of crowns at each end which are to engage the nubs of the adjacent natural teeth, which crowns are integrated with and are usually made as a single unit with the intermediate artificial tooth or teeth. This is quite different and much more expensive than the process of assembling a plurality of individual teeth on a contoured dental arch longitudinal support, as provided by the kit with instructions, which forms part of the present invention. The individual teeth may, after being appropriately spaced, rotated and appropriately mounted to each other, be bonded into their permanent form hereinafter described.

The type of rotation or movement herein referred to of the artificial teeth on the support is done in terms of minutes of arc rather than degrees and in terms of fractions of a millimeter so that such adjustments may readily be made and the bridge becomes custom-made although assembled from individual teeth.

This makes it possible for the dental supply house or laboratory to have a plurality of ready-made teeth on hand of various kinds ranging from incisors, cuspids, and bicuspids to the various molars of various shapes and sizes. As far as colors are concerned, the artificial teeth may be made in such a manner that they may be readily colored to sample color charts as needed or as directed by the dentist. As far as shapes are concerned, various standard shapes and sizes may be stocked; intermediate shapes and sizes may then be created by the dentist. Thus, all grinding on the artificial teeth is done on the model before insertion of the prosthesis. Usually the artificial teeth are ground in the following sequence: the ridge lap area first, the mesial-distal surface second, the lingual surface third and, finally, the incisal edge if necessary. In this way, therefore, as previously pointed out, the dental supply house may have a plurality of teeth which may be placed on the struts or other support and thereby provide a system in which the construction of the bridge is very economical.

The dentist has the choice of using plastic teeth, composite teeth or porcelain teeth in fabricating the bridge.

For example, the versatility of the kit can be applied also to repairing a broken ceramic bridge in the mouth without the need to remove same. In the conventional bridge (ceramic), if it breaks, the whole bridge has to be removed. However, with the permanent one-visit bonded bridge kit, should this occur, it can be repaired in the mouth, without removing the bridge, in one visit at a nominal cost.

STEPS IN THE REPAIR OF A BROKEN CERAMIC BRIDGE IN THE MOUTH USING THE PERMANENT ONE-VISIT BONDED BRIDGE KIT

1. Impression and bite registration is made of the broken bridge and is articulated.
2. Model of broken bridge is waxed up to the correct occlusion.
3. Impression of the waxed-up model is made.
4. A plastic matrix is made of the waxed-up model.
5. The metal frame of broken tooth area is then undercut.
6. The broken bridge area of the plastic matrix is filled with composite and properly seated in the mouth with the area carefully dammed off.
7. The halogen or ultraviolet light will polymerize the composite through the plastic matrix.
8. Result: a repaired ceramic bridge with a composite tooth replacing the broken tooth in the bridge.

In order to aid the dentist in preparing and installing bridges in accordance with the invention, a kit is contemplated, containing detailed, illustrated instructions for the dentist to follow and containing supplies and equipment which are necessary for the procedure and which the dentist may not have at hand.

In carrying out the process and structure of the present invention, notches, rests or grooves are formed on the lingual surface of the natural teeth in the case of the anterior teeth and in the central fossa of the bicuspids and molars. These notches are formed in the teeth on either side of the space which is to be filled by the bridge. The separate artificial teeth are then assembled on the strut or support. The strut or support is adhesively secured in the notches on the lingual surface of the anterior teeth or in the central fossae of the bicuspids and molars.

One of the most desirable and essential elements to be followed in order to avoid destruction of or any unnecessary impairment of the natural teeth is that as far as possible the notches are formed in the enamel and do not penetrate the dentin. It is possible that where the notches or channels are formed in the central fossa, some slight penetration of the dentin may occur. Since a bond to the dentin is not satisfactory, the channels in the central fossae may be undercut in order to provide a secure hold for the composite bond; this affords a mechanical bond. To obtain additional retention for the bond, cavo-surface bevel is made on the enamel margin. This makes possible a chemical bond.

After the notches or steps are formed in the enamel the area of the step is then treated with an etching material, such as phosphoric acid 35% solution which has the effect of etching out the interprismatic cement between the inorganic compounds of the enamel rods. When the interprismatic cement is etched out, a series of voids or micropores communicating with the surface at which the phosphoric acid has been applied are created, providing numerous anchoring tags for the composite bond. The composite bond material may be various bonding materials available to dentists. One type of composite is known as composite bonding material, or the Nuva System, wherein the actual bonding takes place only after activation of the composite bonding material by ultraviolet light, thereby providing the dentist with all the time he may require. Another form of composite to form a bond is chemically activated, providing a finite setting time which may be as little as three minutes, thereby requiring the dentist to work with great rapidity; however, retarding means may be used, such as preliminary refrigeration of the bonding mix or mixing on a refrigerated slab, which may extend the chemically activated setting time to as much as six or more minutes. Where the enamel has been penetrated either because it is only a relatively thin layer in the central fossae of the bicuspids and molars or for other reasons, then the dentist who performs the operation will undercut the tooth substance into the dentin to provide a mechanical lock for the bonding material; and he will also form cavo-surface bevels at the fossa margin of the groove to provide increased enamel surface for anchorage of the bonding material; then, when the bonding material enters, it will not only penetrate into the voids left by the removal of the interprismatic cement but will also flow in the undercut portions. This procedure creates a mechanical bond as well as a chemical bond.

As above pointed out, the teeth may be adjusted with respect to each other prior to the final sealing operation as hereinafter described.

Where an existing live tooth stub exists adjacent the area where additional teeth are to be inserted or where an existing prosthesis is to be removed and the live anchor tooth originally had a crown, but has been ground down and is still a viable tooth, the connection may be made to the anchor tooth in various ways.

One preferred way where the tooth stub is so small that it may be too sensitive, too weak or otherwise unable to receive and support the struts from the prosthesis is to insert what amounts to a protective covering equivalent to a thimble with loops and tags over the tooth stub with the thimble being appropriately grooved on top or circumferentially so that the strut may be connected thereto. Then a finished crown like an isosit may be placed over the thimble to provide an apparently complete tooth. While this thimble may be made of metal and may be secured in any suitable manner, even by soldering to the strut which extends from the prosthetic tooth or bridge, the covering material is a bonding material so that it can at least be adhesively secured over the thimble. This affords retention to the tooth stub and provides a finish to the anchoring stub tooth to make it look like a complete live tooth. The thimble may be formed with surface anchoring tags to provide mechanical retention with the bonding material.

Since adjustment of the individual artificial teeth on the strut or other support requires slight adjustments of only minutes of arc or small fractions of a millimeter, it is possible to have the artificial teeth oriented with respect to each other mounted not only on the strut but even to provide them with matching extensions and recesses so that the artificial teeth may more readily be integrated. Thus the artificial teeth may each be provided on one side with extensions, and on the other side with a corresponding recess so that the teeth may be nested with each other when assembled on the strut and thoroughly integrated with each other. The slight adjustments which are needed to adjust the teeth with respect to each other may nevertheless be made because some very minor amount of play may be provided between each projection and recess. The projections and recesses may have any desired cross-sectional shape—square, rectangular, hexagonal, triangular or circular.

One of the essential objects of the present invention, therefore, is the provision of a dental bridge or prosthesis which may be readily constructed from a plurality of separate teeth assembled in accordance with the requirements of the particular bridge and where the bridge need not be cast or manufactured as a single unitary component initially before it is placed in the mouth; but where the bridge may be unitized and characterized after it is placed in the mouth.

This permits the utilization of the advantages of mass production in at least one portion of the bridge work in that a plurality of artificial teeth of various types and sizes may be manufactured and stocked either in appropriate shades or of material which may be stained to an appropriate shade. Therefore, the bridge may be assembled on the strut or other support from the separate teeth and thereafter the separate teeth unitized as desired or as may be necessary to make a bridge which not only is self-supporting but also coacts to support the individual elements thereof. The material is sufficiently workable that a skilled dentist may make the necessary adjustments.

The individual teeth may be made of whatever material is usually used to make artificial teeth, my preference being isosit teeth. Such a material may be one or more varieties of methyl methacrylate or acrylic resin or composite. The metal struts or support members which support the individual tooth or series of teeth to form the bridge may be a stainless steel 18-8 of any desired cross-section—square, rectangular, hexagonal, triangular or round. The struts may be tubular and therefore telescopic and also available to receive other inserts.

The strut or other support and the composite bond, when completed, coact to provide a structure which is capable of resisting the very high stress which occur during biting and mastication.

It has been found that the bridge according to the present invention is able to withstand compression forces up to 48,000 pounds per square inch. This is superior to dentin, which has a limit of 28,000 pounds per square inch, and is not very much inferior to enamel, which is able to withstand 50,000 pounds per square inch. The tolerance of the bridge is similar to that of bone.

In part because of this feature, and in part because of the shape of the bridge of the invention, an additional important advantage over conventional bridges is obtained. The process of calcification, if unimpeded, will strengthen the bond securing the bridge in position in the mouth. In conventional bridges, the stress causes by mastication, biting, etc. is concentrated on the bond between the bridge and the tooth stubs to which it is secured. This occurs because prior art bridges are able to move slightly in the mouth even after being bonded in place. Such highly localized stresses break up the deposits laid down by the calcification process as they form. The bridge of the present invention, in contrast, both because it is anchored immovably in the mouth and because of its great mechanical strength, distributes the stress of mastication, biting, etc. evenly over the entire structure, rather than concentrating it at a few points. As a result, the calcification deposits are not broken up as they form, and they provide extra strength to the bonds holding the bridge in the mouth. This contributes to bone regeneration.

In the process hereindescribed a plastic matrix may be used. When the prosthetic teeth are placed in position and everything is found to be in correct condition, then appropriate adhesive may be applied to the prosthetic teeth in order to bond them with relation to each other, thereby integrating the bridge. The setting of the entire prosthesis in the mouth is, of course, determined by the location of the prosthesis with respect to the adjacent live abutment supporting teeth which have been formed or shaped in order to receive the extending struts or supports. The adhesive material which bonds the artificial teeth together may be an acrylic resin. The bond to the natural teeth may be effected by the use of an ultraviolet light, or of a halogen light with the "nuva" system or halogen system, which includes material sensitive to both ultraviolet light and halogen light, or any other suitable material.

In order to maintain the teeth in their appropriate relationship to each other until the ultraviolet light or halogen light is applied thereto, a matrix is made of clear copolymer resins of a high molecular weight. When the prosthetic teeth are first fitted and before they are secured in position, a model is made of the patient's mouth. The teeth on the model are then located correctly. The prosthetic device is placed on the model to make sure it is located exactly. An impression is made of the model with the prosthetic teeth in place, and a new stone cast or model is formed. A plastic sheet is then placed over the new model and vacuum shaped by any well known vacuum means so that the sheet is forced to conform to all of the variations in the surface of the new model, thereby forming a negative of the teeth in the patient's mouth with the prosthesis in place.

Thereafter when the acrylic teeth or Isosit teeth or any suitable composite teeth, are lined up in correct position in the patient's mouth and are found to be in proper relationship to each other and to the live teeth, the adhesive, which is a composite which is sensitive to ultraviolet light or halogen light, is placed thereon. The matrix is then placed over the teeth, and short exposures (of the order of 30 seconds) of ultraviolet light or twenty (20) seconds of the halogen light are made by an appropriate light source to the composite in order to polymerize it. This method requires a matrix which is transparent to ultraviolet light or halogen light. When other bonding systems are used, the time control is inherently set by the content of the bonding system rather than at the option of the dentist; but the skilled dentist may work within any reasonable time frame which is available.

In order to enable dentists to familiarize themselves with the procedure for installing the bridge of the present invention, a kit is provided explaining the procedure in detail and presenting numerous figures or, preferably, photographs illustrating the steps of the procedure. This kit also contains certain essential supplies and equipment, such as pieces of stainless steel or the like shaped in different arches sizes and twisted, as is described below. These arch pieces can be cut to length and shaped to serve as the struts, bonding materials and a lamp to provide light to photocure the bonds formed with the bonding material. This kit greatly facilitates the procedure of making and inserting the prosthesis and is described in more detail hereinbelow.

Another important feature of the present invention is that the manufacture and installation of a bridge according to the invention involves no work below the gingival line. Accordingly, the danger of infection is reduced, as is the amount of discomfort experienced by the patient after the installation. This prevents percolation.

The foregoing and many other objects of the present invention will become apparent in the following description and drawings in which:

FIGS. 1–26 are a set of Figures illustrating the procedure of making and installing a bridge according to the invention and preferably constitute the illustrations of a manual, described hereinbelow, containing instructions in this procedure for dentists who wish to use it, the manual constituting part of a kit which is described hereinbelow.

FIGS. 27 and 27A–E show arch-shaped struts for use in carrying out the procedure of the present invention, which struts are included in the dentist's kit described hereinbelow.

FIG. 29 is a view of the teeth in a patient's mouth showing one form of the dental prosthesis of the present invention as used for front teeth.

FIG. 30 is a view corresponding to FIG. 29 but showing another form of the dental prosthesis as used for posterior teeth or molars.

FIG. 31 is a schematic view of the dental prosthesis of FIG. 29 showing the method of interconnection of the prosthetic teeth and the live teeth.

FIG. 32 is a composite Figure showing one form which the teeth of FIGS. 29, 30 and 31 may take.

FIGS. 33, 34 and 35 are successive views showing the method of etching the live teeth in order to remove the interprismatic cement and provide voids or micropores in which the composite used for locating and securing the bridge may hold.

FIG. 36 is a composite view showing successive steps in the manufacture of the prosthesis of the present invention.

FIG. 37 is a plan view of the final matrix which is used to position the prosthetic teeth or bridge in the mouth in order to secure the same in position.

FIG. 38 is an anterior view of the matrix in place over the bridge.

FIG. 39 is a cross-sectional view of the matrix of FIG. 37.

FIG. 40 is a view of a live tooth taken from line 40—40 of FIG. 29.

FIG. 41 is a lingual view of the tooth of FIG. 29.

FIG. 42 is a cross-sectional view of a molar (bicuspid) taken from line 42—42 of FIG. 29.

FIG. 43 is a cross-sectional view of a viable anterior tooth showing a circumferential retention notch.

FIG. 44 is a view corresponding to that of FIG. 43 showing the installation of a crown.

Figure 1:
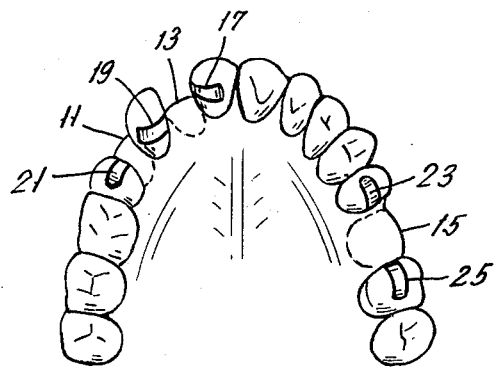

Before a specific description of the invention in connection with the drawings, the steps which are taken in order to perform the operation may be described:

1. Impressions of upper and lower jaws, bite registration and the tooth shade are taken.

2. Casts are made and articulated with bite registration.

3. Plastic or porcelain artificial teeth are selected and accurately ground in for ridge lap adaptation.

4. The artificial teeth are aligned and waxed in position on the articulated model and checked for centric, protrusive and right and left lateral excursions of the bite registration relationship.

5. An impression is taken of the model of step 4, and another work model cast of the waxed aligned teeth is poured.

6. The work model cast is sprayed with silicone lubricant release agent.

7. An accurate vacuum formed index-matrix of a clear copolymer resin of high molecular weight is made. Its unique properties allow it to remain permanently flexible, yet strong and tough enough to hold the aligned teeth in position. This index matrix is set aside for the final alignment and bonding.

8. A horizontal channel is formed mesio-distally on the middle third of the lingual surface of the ground plastic teeth, and an internal metal frame or structure is fitted to a depth of the width of metal bar in the channel previously formed and extending onto the natural abutment teeth. The abutment teeth have each had a horizontal step, recess or rest formed or shaped at the middle third of the lingual surface at right angles to the long axis, to a depth slightly more than the thickness of the strut or support. For porcelain teeth, a gold strut or other suitable metal alloy or support is used. For plastic teeth (methyl methacrylate), one or more stainless steel struts are used, of gauges from 0.030 to 0.060, depending upon the expected stress factors.

9a. Using the previously made index matrix, the plastic teeth are bonded to the metal frame or strut or to each other and added as needed to the ridge lap of the ground in teeth to obtain an accurate ridge lap adaptation. They are then carefully finished and polished.

9b. If porcelain teeth are desired, then a kiln capable of firing porcelain at approximately 2200° F. is necessary. This may not be available at the dentist's office. Where it is not available, then the dental laboratory must for that purpose be introduced into the procedure. The procelain teeth are bonded to the metal strut or frame (Jelenko white gold-Olympia or appropriate gold) and carefully fired in the oven to obtain accurate ridge lap adaptation, and are carefully finished and glazed.

When plastic or composite teeth are used, the dentist can perform all the laboratory procedures himself and thus bypass the dental laboratory.

The bonded bridge is now ready for insertion into the mouth. The success of the bonded bridge depends upon complete abutment tooth isolation and freedom from salivary contamination during insertion.

CLINICAL PROCEDURE

In addition to the foregoing apparatus the following equipment is needed to install the bridge of the invention in the mouth:
1. Distilled water spray syringe or hand spray bottle;
2. Air syringe free of oil mist and water;
3. Saliva evacuator system;
4. A dental engine for prophylaxis and removal of old fillings or to form lingual rest;
5. Lip and cheek retractors;
6. Dri-angles placed over Stenson's duct;
7. Rubber dam.

Any tooth in the mouth may be replaced with this procedure.

Referring now to the drawings, FIGS. 1-26 are a set of illustrations included in a manual which is part of a kit which is to be provided to dentists and which contains all necessary instructions for carrying out the procedure of the present invention, as well as certain supplies and equipment required for the procedure and not commonly found in the usual dentist's office. Besides the illustrations and accompanying instructions arranged in the form of a brochure, the kit includes a number of generally arch-shaped pieces of metal or another material to be cut to length and used as struts in constructing bridges according to the present invention. The kit also includes materials for bonding the bridge in the mouth, six vials of different shade coating material for coating the struts, so that the prosthesis can be exactly matched in color to the patient's natural teeth, a tool for shaping the arches to the exact shape to fit the patient's mouth, and a halogen or ultraviolet light for polymerizing the coating material. A brush or other appropriate applicators may be included together with instruments for packing the composite bonding material into the grooves in the natural teeth which receive the strut. The coating material not only matches the struts in color to the natural teeth, but also prevents the struts from being discolored due to chemical reaction of the bonding material. The coating material is also for coating the tools in use, since the materials of which these are made react with the bonding material.

Referring in sequence to FIGS. 1-26, illustrating the instructional brochure, FIGS. 1-4 are different views of the patient's mouth (represented for purposes of the brochure by a model). For purposes of illustration, it is assumed that the fifth, seventh and fourteenth teeth 11, 13, 15 of the patient's upper jaw (counter clockwise from the lower left-hand corner of the Figure, which corresponds to the rear right corner of the mouth) have been removed and are to be replaced with a prosthesis according to the invention. FIG. 1 clearly shows the locations on the patient's remaining natural teeth where markings have been made to indicate the proper location for indentations which will receive the struts of the prostheses. In the example illustrated, one prosthesis will be provided to replace the fifth and seventh teeth 11, 13 (the first right bicuspid and the right lateral, respectively), and a second prosthesis will be provided to replace the fourteenth tooth 15 (the left first molar). To receive the strut of the first prosthesis, a groove will be formed in the lingual surface of the right central 17 and the right cuspid 19, and a groove or notch will be formed in the central fossa of the right second bicuspid 21. Similarly, notches have been formed in the central fossae of the left second bicuspid 23, and second molar 25 to receive the strut of the second prosthesis. As can be seen, all of the indentations formed for the prothesis struts are located entirely supragingivally, which is contrary to the requirements of conventional mouth restoration techniques to which dentists are accustomed. Accordingly, the dentist must pay special attention to this point until he is thoroughly accustomed to working in this manner. It is highly advisable that the dentist mark the exact location of each groove preparatory to cutting it, as shown in FIGS. 1-4, so that he will have a guide during the actual cutting operation.

Figure 2:
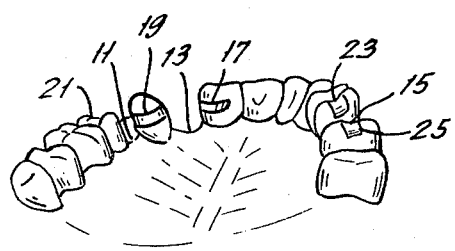

FIG. 2 is a supragingival outline of the tooth preparation, i.e. the markings made on the patient's natural teeth in which the grooves for the struts are to be made.

Figure 3:
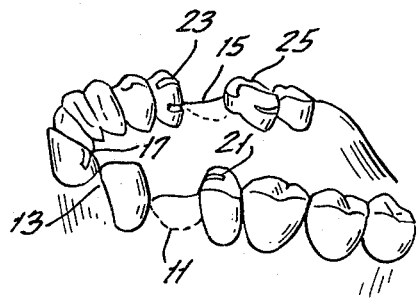
Figure 4:
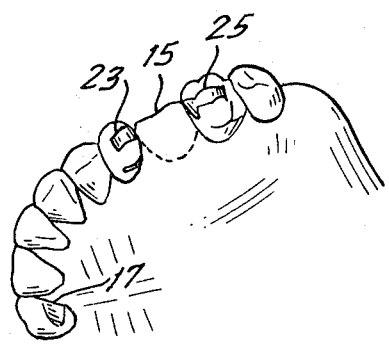

FIGS. 3 and 4 are a lingual view and an occlusolingual view, respectively, of the tooth preparation. During this stage, also, the proper shade of coloration for the artificial teeth is determned, and artificial teeth of the proper shade matching that of the natural teeth are selected for the prosthesis.

Figure 5:
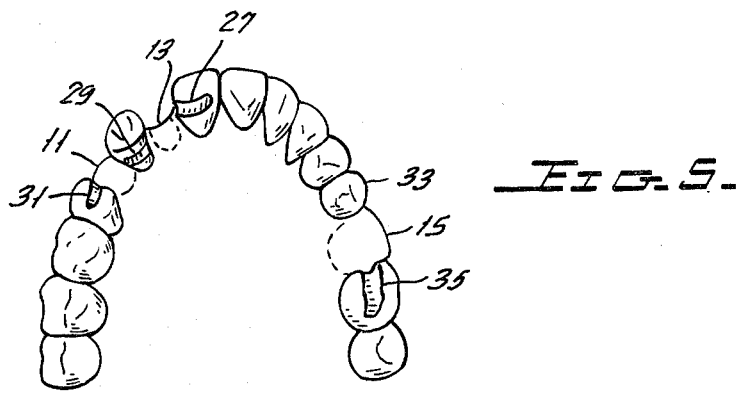

FIG. 5 shows the patient's teeth after the grooves for the struts have been actually cut. The steps 27, 29 formed in the lingual surface of the right central 17 and right cuspid 19, as well as the recesses 31, 33, 35 formed in the fossae of the right second bicuspid 21 and the left second bicuspid 23 and second molar 25 are clearly visible. These steps and recesses are cut approximately to the depth of the dental-enamel junction. It is possible, however, in the case of a recess formed in a posterior tooth, that the cut will accidentally be made sufficiently deep to extend into the dentin. In this case, the dentist undercuts the enamel slightly and provides the recess with a cavo-surface bevel, to ensure a good bond, as will be described in detail below. Such undercut preparation could also be used in the anterior teeth, if it appears advantageous to do so.

Figure 6:
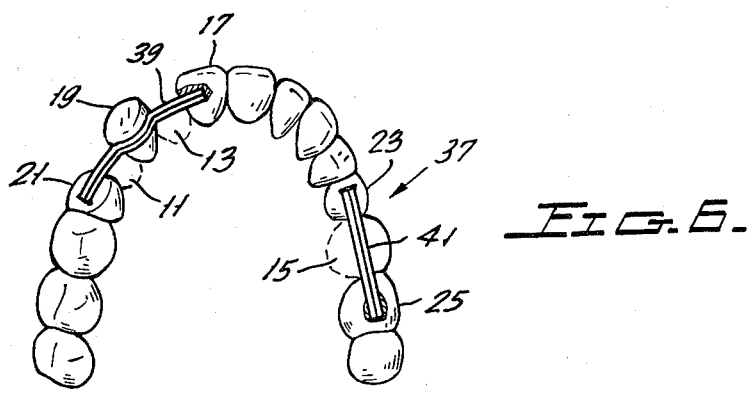
Figure 27:
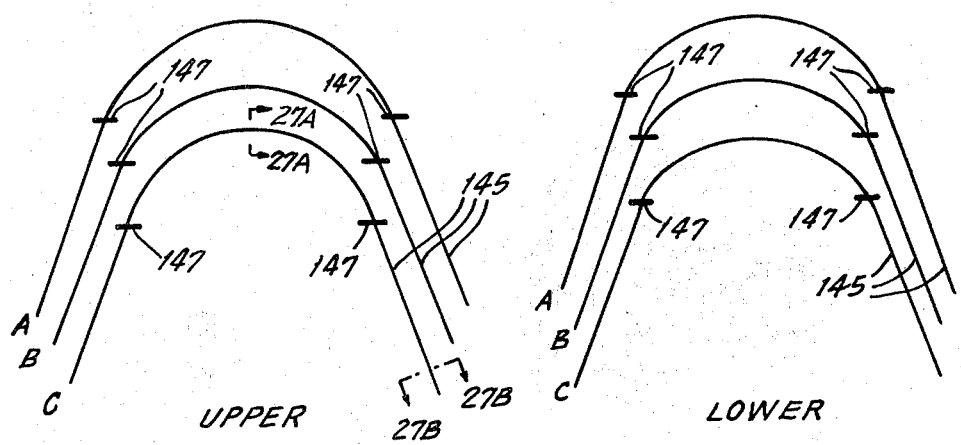
Figure 28:
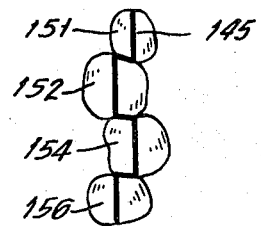
FIG. 28 shows the adaptation of a strut for use with natural teeth which are not properly aligned with each other in the mouth.

FIG. 6 shows a laboratory model 37 of the patient's jaw made after the grooves have been cut. The dentist now prepares the prosthesis struts 39, 41, shaping and cutting them to the proper length for use in the particular patient's mouth, and using the model 37 to ensure that the struts 39, 41 are properly formed, as shown in FIG. 6. As was stated above, the kit with which the dentist is provided includes a number of arches made preferably of stainless steel, from which the struts are fashioned. Each arch has approximately the proper shape to fit a full mouth, as is shown in FIGS. 27 and 28. The dentist selects the portion of the arch which most nearly fits the portion of the patient's mouth in which it is to be used. Using a tool included in the kit, he shapes the selected portion of the arch to the exact shape desired and cuts it off to the proper length. Since the dentist can, by virtue of this kit, perform this procedure in his own office laboratory, it will be appreciated that it is no longer necessary for him to have recourse to an outside laboratory, thus reducing both the cost and the number of visits required for the manufacture and insertion of the prosthesis.

Figure 7:
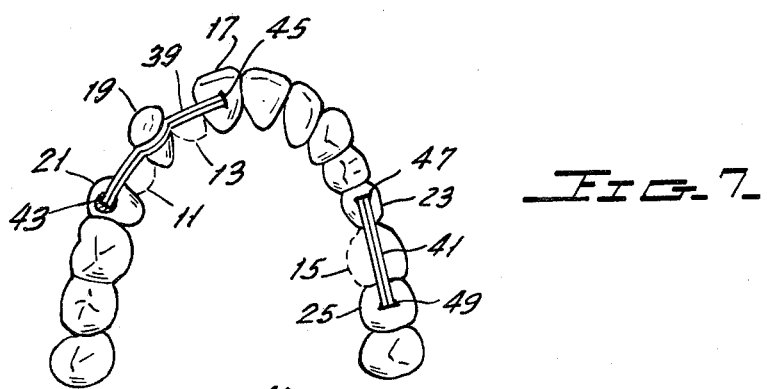

FIG. 7 is an occluso-lingual view showing the struts or bonding bars waxed in position 43-49 on the laboratory impression 37 of the patient's mouth. By working with a model at this stage, the dentist is able easily to give the bonding bars exactly the right shape, and to position the artificial teeth thereon in exactly the correct position. It should be noted that the struts 39, 41 are both positioned and contoured so that when the prosthesis is bonded in the patient's mouth, the struts 39, 41 will lie in infra inclusion, i.e. below the occlusal plane where the upper and lower teeth would meet. The bonding bars 39, 41 are work hardened during the contouring procedure, to obtain the proper bite relationship.

Figure 8:
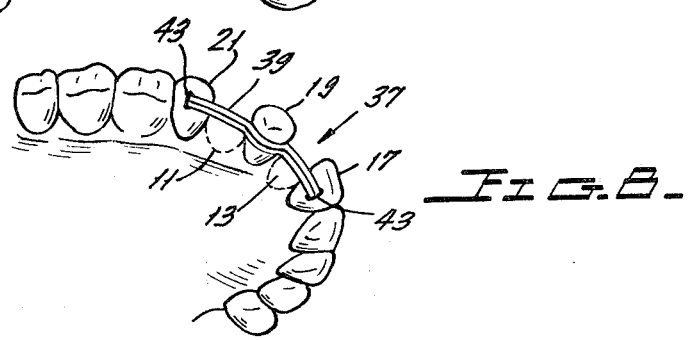

FIG. 8 is a lingual view of the laboratory model 37, showing one bonding bar 39 waxed in position thereon.

Once the struts or bonding bars 39, 41 have been given the proper shape, they are ready to have the artificial teeth secured to them.

Figure 9:
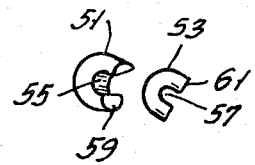

FIG. 9 shows two plastic teeth 51, 53, each having a channel recess 55, 57 to receive a bonding bar. In the artificial teeth 51, 53 shown, which are posterior teeth, the channel 55, 57 formed in what will be the underside 59, 61 of the tooth 51, 53 when it is in place. In the case of anterior teeth, the channel is formed on the lingual side, rather than the ridge lap surface. The artificial teeth are selected from a stock thereof maintained either by the dentist or by an outside laboratory or dental supply house, and are selected to match the shade of the patient's natural teeth as nearly as possible.

The artificial teeth are ground by the dentist to the exact size and shape necessary and are then waxed into place on the bonding bars 39, 41 while the latter are still waxed in position on the laboratory model 37 of the patient's mouth. By having the bonding bar mounted on the model in this fashion, the dentist is able to grind the artificial teeth to the correct shape easily and exactly.

Figure 10:
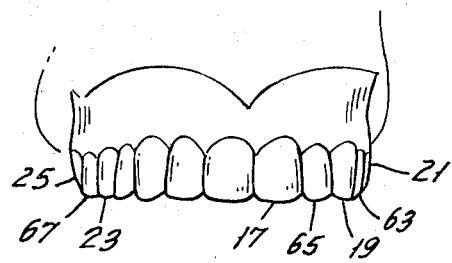
Figure 11:
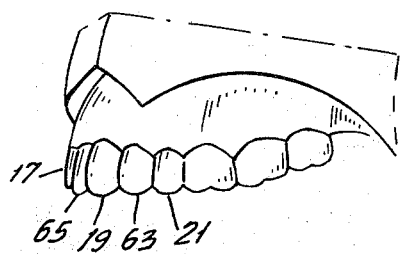
Figure 12:
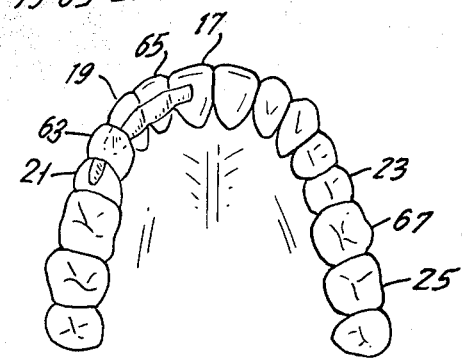

FIGS. 10-12 are three views of the laboratory model 37 with the artificial teeth 63, 65, 67 waxed in position on the bonding bars 39, 41, FIG. 10 being a front view, FIG. 11 a buccal view of the artificial left first molar 67 in position in occlusion, and FIG. 12 being an occlusal view showing all three artificial teeth 63, 65, 67.

Figure 13:
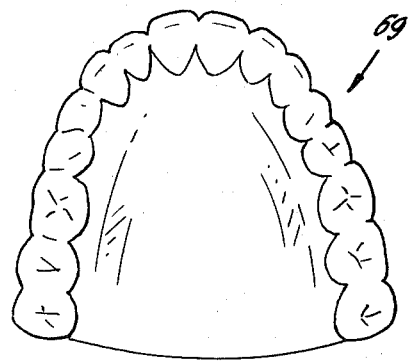

When the artificial teeth 63, 65, 67 have been ground to the proper shape and are waxed in position on the laboratory model 37, as shown in FIGS. 10-12, the dentist prepares a duplicate cast from the master laboratory model 37. The duplicate cast 69 is shown in FIG. 13.

Figure 14:
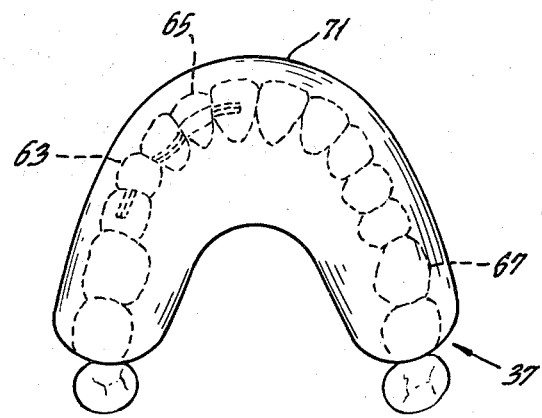

A plastic index matrix 71, shown in FIG. 14, is then made from the duplicate cast 69. The purpose of this matrix 71 is to maintain the artificial teeth 63-67 and the bonding bars 39, 41 in position relative to each other during the bonding operation. Quick-setting acrylic of the proper shade is used to effect the bonding of the plastic teeth 63-67 to the bonding bars 39, 41.

Figure 15:
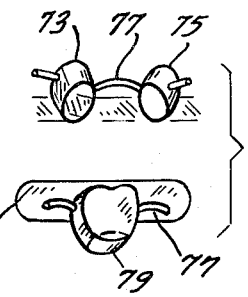

FIG. 15 is a composite view for illustrating the process clearly. The upper portion of FIG. 15 shows a reproduction representing two of the patient's natural teeth 73, 75 (i.e. not prosthetic teeth) with a binding bar 77 secured to them in the position which it will ultimately have relative to them when the prosthesis has been finally inserted and bonded in the mouth. The lower portion of FIG. 15 shows a prosthetic tooth 79 which will ultimately be fixed in place between the two natural teeth 73, 75 shown in the upper part of the Figure. The prosthetic tooth 79 shown in the lower part of FIG. 15 is shown secured to its bonding bar 77 by means of quick-setting acrylic 80.

Figure 16:
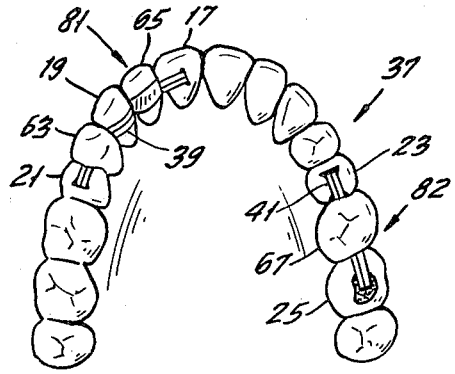

FIG. 16 shows the master laboratory model 37 with the prostheses 81, 82 in place thereon. The prosthesis 82 represented in FIG. 15 appears at the right-hand side of FIG. 16.

Figure 17:
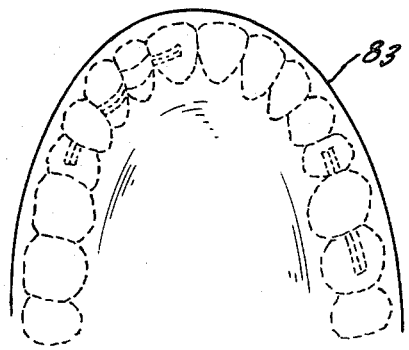

Before the prostheses 81, 82 are moved from the laboratory model 37 to the patient's mouth, a second plastic matrix 83 is formed on the model 37, as shown in FIG. 17. This matrix 83 will be used for bonding the prostheses 81, 82 in the mouth. Note that it is cut back away from the gingival surface at both the buccal and the lingual side 85, 87 to within about 2 mm of the occlusal or biting plane, as shown in FIG. 18.

Figure 18:
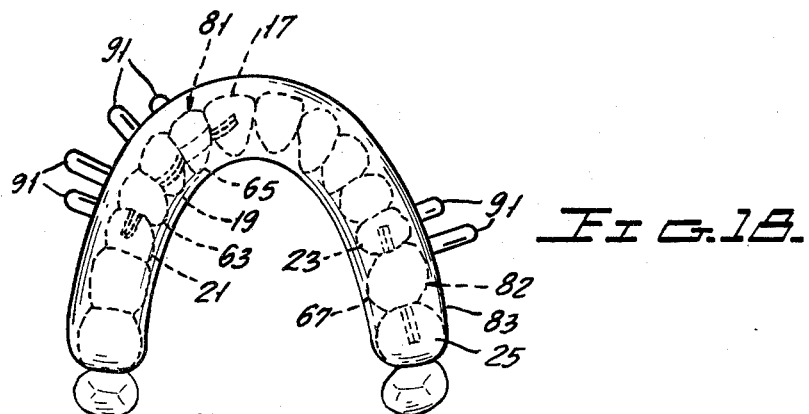

FIG. 18 shows the matrix 83 of FIG. 17 cut back, as described above, and placed in the patient's mouth. A rubber dam 89 is placed between the index matrix 83 and the roof of the mouth, where it is held in place by plastic gingival wedges 91. The purpose of the rubber dam 89 is to keep the natural and the artificial teeth absolutely dry, since the bonding process cannot be carried out in a wet environment. The plastic gingival wedges 91, which are placed between each artificial tooth and the adjacent natural teeth (i.e. in each area in which a bonding is to be effected) are to prevent the bonding material from approaching the gingival surfaces, to prevent problems with pyorrhea and periodontics. This precaution is necessary because the composite material used for bonding is very irritating to gingival tissue.

Figure 19:
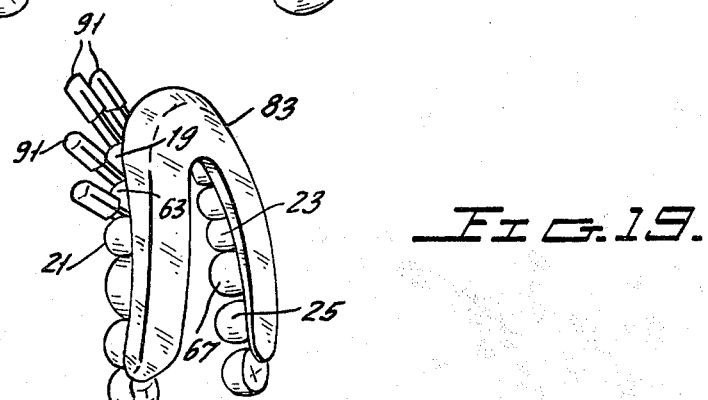
Figure 19A:
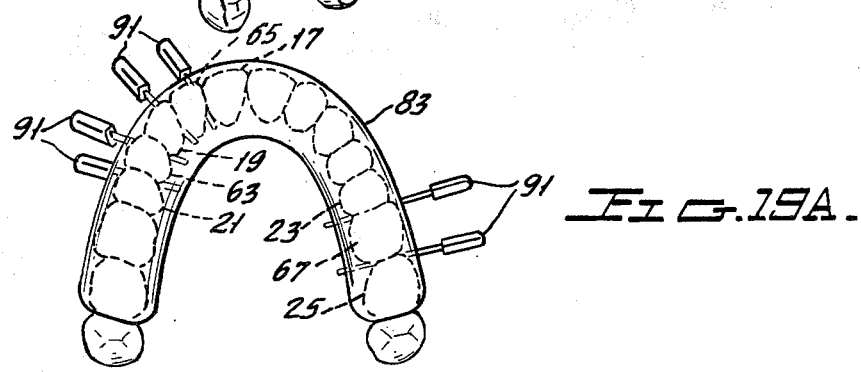

FIG. 19 is another view of the patient's teeth with the prostheses 81, 82, the plastic index matrix 83 and the gingival wedges 91 in place. In order to bond the prostheses 81, 82 permanently in place, the dentist carries out the following steps. First he cleans the abutment teeth 17-25, i.e. the natural teeth immediately adjacent to the prosthetic teeth 63-67, with flour of pumice. He then washes them with water and dries them thoroughly. All exposed dentin is then covered with a layer of calcium hydroxide, after which the calcium hydroxide layer is covered with a composite sealant to prevent the water-soluble calcium hydroxide from dissolving during the following steps. The composite sealant is photocured to complete the protection of the calcium hydroxide. The photocuring step is preferably carried out with a halogen lamp or ultraviolet light 93, which may be supplied to the dentist as a part of the kit. I prefer halogen light to ultraviolet light at present because, while ultraviolet light penetrates the composite materials now in use to a depth of about 1.5 mm, halogen light can penetrate them to a depth of 4 mm, ensuring complete polymerization thereof. The photocuring step is shown in FIG. 19a.

Figure 20:
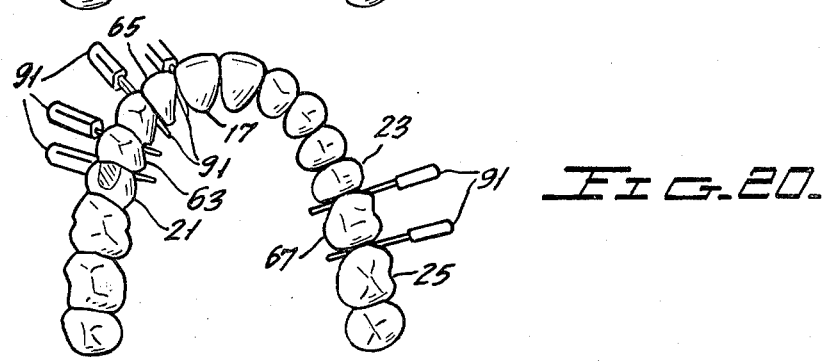

During the photocuring step, the enamel cavo-surface margins of all abutment teeth are conditioned with 35 percent phosphoric acid, which enables these surfaces to form a much stronger chemical bond than would otherwise be possible. The abutment teeth are then washed with water and thoroughly dried with air which must be entirely free both of oil mist and of water, as the presence of either of these interferes with the bonding. The exposed metal of the bonding bar 39, 41 is then masked with a coating material which prevents it from reacting with the bonding material. If this precaution is not taken, the bonding material will not mask the strut. A layer of the composite bonding material is then deposited in the notches and grooves 27-35 prepared in the abutment teeth for the struts 39, 41, and the prostheses 81, 82 are then seated in the mouth. The bonding bars 39, 41 are then covered with bonding material, the matrix 83 is replaced in the mouth, and the composite bonding material is then photocured. The halogen lamp or ultraviolet light 93 is used. After the second photocuring step, the matrix 83 is removed, leaving the patient's mouth as shown in FIG. 20. The wedges 91 and the rubber dam 89 are then removed, completing the procedure.

Figure 21:
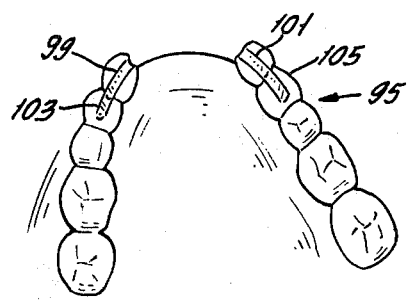
Figure 22:
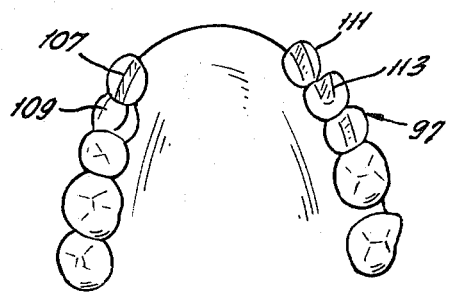
Figure 23:
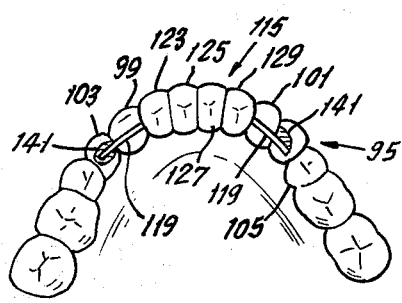
Figure 24:
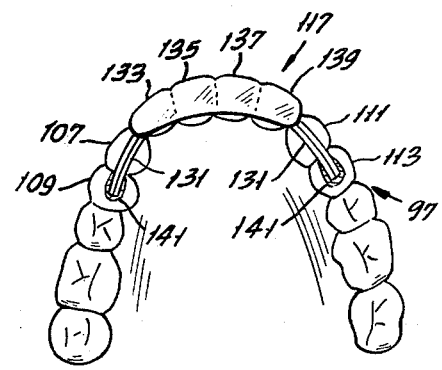

FIGS. 21-26 show a clinical application of the procedure described in connection with FIGS. 1-20. FIGS. 21 and 22 show models 95, 97 of the lower and the upper jaws, respectively, of a patient missing eight teeth, four in the upper jaw and four in the lower. In both Figures, the lingual surface of the left and right cuspids is provided with a step 99, 101, 107, 109 to receive a bonding bar, and the occlusal surface of the left and right first bicuspids 103, 105, 111, 113 is provided with a groove formed in the central fossa thereof for the same purpose. FIGS. 23 and 24 show the same models 95, 97, with the addition in each case of a prostheses 115, 117 according to the present invention. In FIGS. 23 and 24, the prostheses 115, 117 comprise a bonding bar 119, 131 having four anterior teeth 123-129, 133-139 mounted thereon and received on the seats provided for them on the abutment teeth 99-113. The prostheses 115, 117 are held in place by wax 141. It will be noted that the bonding bar 119 in FIG. 23 is made of a single piece of stainless steel, while that in FIG. 24 comprises two rods joined side-by-side, as by welding.

Figure 25:
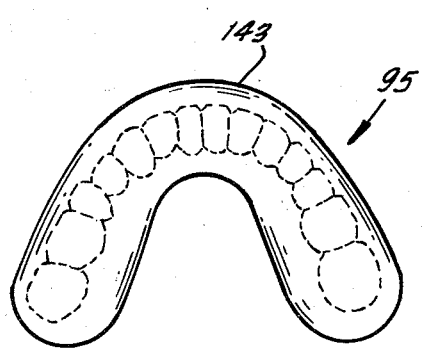
Figure 26:
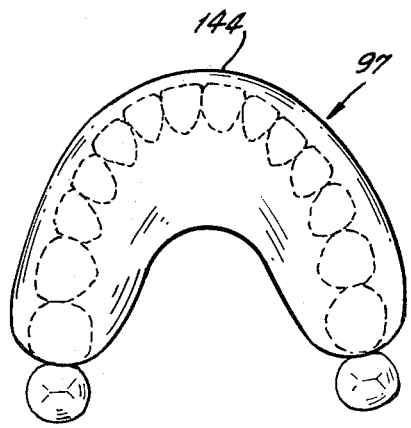

FIGS. 25 and 26 show the models 95, 97 with the prostheses 115, 117 mounted thereon, as in FIGS. 23 and 24, respectively, with the first plastic index matrix 71 in position thereover. This matrix 71 is used in each case to maintain the artificial teeth in position relative to the bonding bar for bonding thereto.

This completes the description of the procedure as set forth and illustrated in the instructional brochure included as part of the kit which is supplied to the dentist.

Figure 27A:
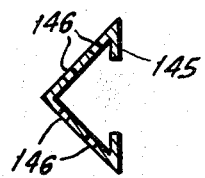
Figure 27B:
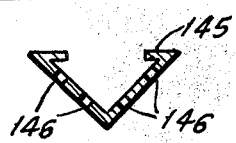

In addition to this brochure, the kit also includes sets of arches 145 made preferably of stainless steel which can be shaped and cut to serve as the strut or bonding bar of a prosthesis. The arches 145 are provided in three sizes, small, medium and large, and in two shapes, one adapted for use with upper teeth, as shown in the left-hand portion of FIG. 27, and one adapted for use with lower teeth, as shown in the right-hand portion of FIG. 27. The letters "A", "B" and "C" indicate the three sizes of each shape of arch. The arches 145 shown in FIG. 27 and in cross-section in FIGS. 27A and 27B are designed to be cut to length for use as a strut which will be received in a natural tooth, especially an anterior tooth. This arch 145 has a hollow triangular cross-section in order to increase its mechanical strength. One side of the triangle is left partially open to allow the hollow interior to be filled with composite bonding material, as is explained more fully below in conjunction with FIG. 40A. The remaining two sides are provided with apertures 146, which permit the formation of a still stronger bond to the tooth. As can be seen from the section lines 27A—27A and 27B—27B of FIG. 27 and from FIGS. 27A and 27B, the arch 145 is provided with a 90° twist at two symmetrically located points 147. A strut or bonding bar to be received in the anterior teeth is cut from the portion of an arch 145 lying between the two twist points 147, while a strut to be received in the central fossa of one or more posterior teeth is cut from a portion of the arch exterior of the twist point 147. If a strut is to be received both in an anterior tooth and in a posterior tooth, then it is cut from a portion of the arch 145 containing the twist point 147, so that the strut includes two portions which are twisted 90° relative to each other about the longitudinal axis of the strut. As a result of this feature, the portion of the strut which is received in a rest or groove formed in the lingual surface of an anterior tooth is received therein apex-first, i.e. with the open side of the strut facing the tongue, and the portion of the strut that is received in a notch formed in the central fossa of the posterior tooth is also received therein apex-first, i.e. with the open side of the triangle facing upward if inserted in a tooth in the lower jaw and downward if inserted in a tooth in the upper jaw. This arrangement allows the bonding bar to be bonded with maximum strength to each tooth, whether anterior or posterior, in which it is received.

Figures 27C, 27D:
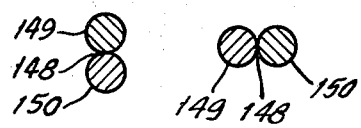
Figure 27E:
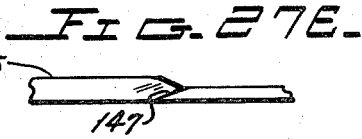

The kit may include arches 148 comprising two wires 149 and 150 welded together side by side for making bonding bars at least one end of which is to be received in a notch formed in the central fossa of a posterior tooth. Two cross-sections of a two-wire arch 148 are shown in FIGS. 27C and 27D, which views correspond respectively to the cross-sections of FIGS. 27A and 27B. The two-wire arch 148, like the triangular cross-section arch 145, is twisted by 90° to allow bonding bars cut from it to be received in the optimal manner in either anterior or posterior teeth.

It will be understood by those skilled in the art that the dentist, in cutting off a length from the arch to form a strut, will also shape the cut-off portion with a tool of a well-known type, for example a three-prong pair of pliers, to fit the patient's mouth exactly. One example of a strut shaped in this manner is shown in FIG. 28, in which the strut made from the arch 145 has been provided with a series of six sharp, angular bends to accommodate irregularities in the location of the patient's teeth 151, 152, 154 and 156. In the example shown, the four teeth 151, 152, 154 and 156 are posterior teeth, and strut 145 is received in notches formed in the central fossa thereof. In the example shown, tooth 152 displays a buccal excursion, while its neighbor 154 displays a lingual excursion, teeth 151 and 156 being properly located. In order for the strut 145 to be received in the notches formed in the central fossa of each of the four teeth 151, 152, 154 and 156, it must be bent in the manner shown. This type of procedure is well known to the dentist.

The kit also includes the composite sealant material which is used to effect the bonds, as well as the quick-acting acrylic. If the arches are made of stainless steel, then clay material must also be supplied for application to the bonding bar to mask it, as described above. Preferably, the coating material is provided in six different shades, from which the dentist selects the one which most nearly matches the color of the patient's natural teeth. A halogen light is also provided for use in photo-curing the sealant material. In the event that the sealant material used by the dentist is the fast-acting chemical bonding material referred to above, it will be understood that neither the halogen lamp nor an ultraviolet lamp is required. Finally, the kit also includes a pair of pliers which is specially designed for bending the arches to the exact shape required.

The arches 145, 147 are preferably made of a chemically resistant version of stainless steel, for example Allegheny Metal 18-18 M, Type 316, which is available from Allegheny Ludlum Steel Corporation.

A second example will now be described.

EXAMPLE: REPLACEMENT OF THE UPPER LEFT CUSPID

1. In the event an occlusal filling is present in the upper left first bicuspid, remove it and slightly undercut the buccal and lingual walls of the cavity and make a dovetail lock and a cavo-surface bevel with a horizontal step or rest on the upper left lateral.

2. Isolate teeth and then brush the abutment teeth using flour of pumice or zircate paste. No compound containing glycerine should be used, since it will prevent proper bonding adhesion.

3. Etch with a tooth conditioner which is a 35% phosphoric acid on a cotton pellet with a dabbing motion for one (1) minute to etch both abutment teeth.

4. Wash abutment teeth with clear water. Never use mouth wash spray, since it will prevent proper bonding.

5. Dry the abutment teeth carefully with air free of oil mist and water. Check air blast on mouth mirror; if it fogs the mirror, oil or water is present and will prevent bonding. The teeth, when properly dry, will have a dull white appearance following etching.

6. Place three layers, the first of Pulpdent calcium hydroxide containing cellulose, the second of Dycal calcium hydroxide and the third of carboxylate cement.

7. Place composite bonding seal over these three layers and cover the dull whitish appearance of the abutment teeth and polymerize (by utilization of ultraviolet light or halogen light) for 30 seconds for each location of the bonding composite. If halogen light is used, each exposure should be about 20 seconds. Place the artificial tooth, to which the metal strut or support has previously been bonded, with the extensions or ends of the strut resting on the prepared abutment teeth by means of the plastic index matrix.

8. Remove the matrix.

9. Place composite filling material under and over the metal extensions and carefully cover the metal. Anatomically shape and contour the bonding composite, making sure that no overhang exists, that the previously prepared cavity is covered and that the metal extensions lie appropriately in the left first bicuspid and the lingual step or rest area of the upper left lateral. Place the index matrix in position.

10. Hold the index matrix firmly in place and, using the ultraviolet or halogen light, polymerize for 60 seconds, moving the light over the lingual and occlusal surfaces of the lateral and first bicuspid. The ultraviolet or halogen light will penetrate the clear plastic matrix index and polymerize the composite filling material.

11. Remove the plastic matrix index and then polymerize for an additional 30 seconds over each area where the composite filling material has been placed (20 seconds if halogen light is used).

12. Isolate the bridge and abutment teeth; remove the flash, and feather edge the composite sealant clean with zircate or flour of pumice; wash, dry and cover with composite sealant to give a permanent glaze finish. The gingival margin ends supragingivally.

13. Use a damp gauze sponge to wipe composite to remove methyl methyacrylate to prevent sensitization.

14. Dismiss the patient and recall in a week to check the bite.

CAUTION: At all times throughout the foregoing procedure, isolation of teeth free from salivary contamination is essential.

The advantages and objects attained by means of this procedure are:

1. This novel process and structure decreases the cost of dental care in mouth restorations.

2. Mutilation (grinding) and drilling for tooth preparation in bridge construction are eliminated.

3. The dependency of the dentist on dental laboratories or denturists is eliminated or at least reduced. This is particularly true when using plastic or composite teeth.

4a. A dental bridge can be made from (a) plastic, (b) porcelain or (c) composite.

4b. Stainless steel, gold materials or other metal alloys may be used for the internal structure of the bridge. Composite teeth may thus be made by pouring composite into a mold with the horizontal internal strut or support embedded in the body of the tooth with extensions in female and male members. This simplifies the technique.

5. Artificial teeth may be purchased made out of the plastic, porcelain or composite materials.

6. The extensions may be shortened to fit into the female embedded sections which will have horizontal tubes in the body of the (plastic) tooth to take male extensions 0.036–0.060. These tubes and corresponding extensions may be round, square, triangular or of other appropriate cross-section, as shown in FIG. 32.

7. In the case of the four anterior teeth (FIGS. 29 and 31), the square bar members are inserted into the four teeth and contoured; the extension rests distally on the lingual step of the cuspid (canine) and the central fossae of the first biscuspid on each side.

8. The above extensions are then bonded to the abutment teeth and the bite checked and adjusted.

9. The bridge requires one visit to place and bond in the mouth after the initial impressions are taken.

10. Since this technique does not extend or impinge on the crevicular space, it prevents periodontitis and pyorrhea.

Referring now to the remaining drawings, the prosthetic structure of the present invention may readily be seen in FIGS. 29, 30 and 31. In this structure the bridge 153 of FIG. 29 comprises a plurality of artificial teeth 155, 157, 159, 161, each having an opening 163 therein as seen in FIG. 32 which receives the strut support 165. The openings 165 as seen in FIG. 32 may have various shapes which may be rectangular, triangular, square or round. The rectangular shape appears at the opening 165 in FIG. 32, the triangular shape at 167, a square shape at 169 and a pair of round openings at 171. It should be understood that a plurality of supports 165 may be used and the pair of round openings 171 are utilized in connection with such a plurality of supports. Where the supports are rectangular or square a pair of supports may be dimensioned so that they fit through the rectangular or square openings without the necessity for additional such openings. This, of course, is at the option of the dentist. The strut or support 165 as seen in FIGS. 23 and 22 extends beyond the plurality of teeth where the strut or support is to be interconnected with adjacent front teeth. As previously pointed out, the adjacent front tooth 173 is notched at 177 on the lingual side. The notch has a generally triangular cross-section and is defined by a single surface extending in the buccal direction and a single surface extending in the inclusive direction with respect to the anterior tooth. (See FIG. 40). Where the connection is to be made to a molar 179 (see FIG. 42) the central fossa 181 is shaped as shown to form the groove 183.

In the view showing the single molar of FIG. 42 a pair of bars 205 and 209 are shown. The construction of the bars which interconnect the artificial teeth 155, 157, 159, 161 may as above pointed out be of a cross-sectional shape matching the openings 163, 167, 169 or 171. In FIG. 32 the bar is shown as rectangular in cross-section to match the opening 163. The supports, as shown in FIG. 42, may be a pair of bars or even a larger number depending on the structure of the patient's mouth and the structure and condition of the adjacent teeth.

As seen in FIG. 30 the bridge which is used where molars are required will consist of the replacement teeth 185 and 189 cooperating with the adjacent teeth 191, 193 and 195.

A single anterior tooth replacement 197 is shown in FIG. 8 utilizing the procedure indicated in connection with FIGS. 29, 30 and 31.

As previously pointed out, various preparatory steps may be performed. But before the teeth are shaped as shown in FIGS. 40 and 42, either on the lingual side of the smaller teeth or in the central fossae of the larger teeth, an impression is taken of the tooth structure. The first master matrix is made on the cast made from this first impression. The artificial teeth 155, 157, 159, 161 in the number required are then selected and arranged on the bar 165 which may be a metal or composite bar as already described. The artificial teeth are appropriately shaped and adjusted with respect to the previously made cast and inserted therein to determine that they are in correct position. The bridge is placed on the cast and appropriately positioned. Then, as pointed out in the series of steps above listed, a plastic sheet is vacuum formed on the cast to provide a negative or matrix of the structure as it should appear in the mouth (see FIGS. 37, 38 and 39). At an appropriate time which may have occurred even before the mold is made, but certainly before the final bridge is placed in position, the enamel of the shaped adjacent abutment teeth is etched by the phosphoric acid application above referred to in order to provide a surface which will readily accept the bond and be integrated therewith. This particular process is a known process and is shown and described in FIGS. 33, 34 and 35 which are taken from the literature on the subject and included herein for the sake of completeness.

Figure 40A:
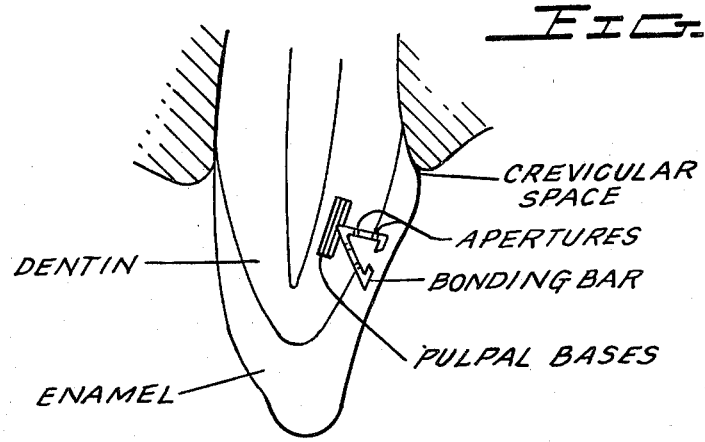
FIG. 40A is a cross-sectional view of a live tooth, showing the bonding bar received in a groove, rest or notch formed in the lingual surface of the tooth.
Figure 45:
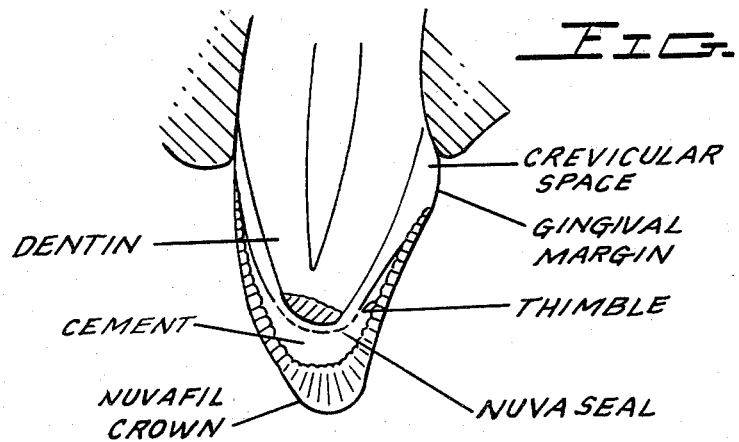
FIG. 45 is a view corresponding to that of FIG. 42 shown in cross-section the installation of a thimble on a fractured tooth or one previously ground to a stub in which the enamel has been removed.

In the event that the dentin has been penetrated during formation of the groove, rest or notch in the tooth surface, the following procedure is used to protect the pulp from the composite bonding material, which is highly irritating to the nerve. A three-layer base (identified by the legend in FIG. 40A) is provided for the bonding bar in the tooth to ensure that there is no contact between the composite bonding material and the pulp. This three-layer base is formed, as is shown in FIG. 40A, by first applying a layer of calcium hydroxide containing cellulose, for example Pulpdent calcium hydroxide, then applying a second layer which comprises calcium hydroxide containing a hardening agent, for example Dycal calcium hydroxide, and finally applying a layer of carboxylate cement. This combination of three layers of the materials specified and applied in the stated order will effectively prevent contact between the pulp and the composite bonding material used to hold the bonding bar in place.

Thereafter the bridge is placed in the patient's mouth with the bar 165 in appropriate engagement with the shaped sections 177 or 183 (see FIGS. 40, 40A, 41 and 42) and with one side of the triangular cross-section of the bonding bar substantially perpendicular to the longitudinal axis of the tooth. By this time the bar has been trimmed to the right length by reference to the cast which had previously been made and the teeth 155, 157, 159, 161 of FIG. 29 or the teeth 185 and 189 of FIG. 30 have been appropriately adjusted. Final adjustments are made with the teeth in the mouth. Such final adjustments if required are so minute as to make it unnecessary to make another matrix. When the bridge is placed in position, an appropriate composite known as composite bonding material is applied and the matrix is placed in position to ensure perfect alignment of all the parts. The matrix is a plastic which is transparent to the ultraviolet or halogen light and the composite bonding seal is a material which will set on the application thereto of ultraviolet or halogen light. The ultraviolet or halogen light gun is then aimed so that the ultraviolet or halogen light passes through the positioned matrix to the areas where the composite bonding material is located and causes the composite bonding material to set and the bridge to be accurately positioned.

In FIG. 32, the bridge of the present invention has been shown with the addendum of the recesses 199 shown in dotted lines and projections 201 on opposite sides of each tooth, so that a projection 201 from one tooth may enter a recess 199 of the adjacent tooth. This provides for further integration and mechanical intersupport of the artificial teeth in the final bridge, thereby strengthening the final bridge. While it is not essential to provide such an arrangement, it may be highly desirable to be so since the assembly of the bridge is made from individual teeth. End teeth for any bridge may be provided without the extension 201 or recess 199; or the extension 201 may be removed and the recess 199 bonded in by the dentist with an appropriate material such as composite or acrylic resin.

FIGS. 37 and 39 are respectively a plan view and a cross-sectional view of the matrix 203 which has been above referred to; such matrices are known but are included herein for purposes of completeness. FIG. 38 is an anterior view of the matrix in position on the teeth and bridge.

By this means, therefore, it will be seen that a simplified operation is provided with minimum interference with the adjacent teeth. The bridge is arranged so that instead of being originally a single unit cast and created to order as a single unit, it may be assembled from a number of separate elements which may be stocked. This decreases the cost of the bridge since, until the final assembly and adjustment, mass production methods are available and stock items may be used.

In other words, the dental supply house will have a stock of separate teeth of various sizes for various portions of the mouth, stocks of separate supports or bars and will provide these to the dentist in accordance with his requirements so that he may assemble them on the bar to form the bridge. The bar itself as seen in FIG. 25 may be appropriately marked at the lines 50 or shaped to provide a guide for the dentist. The dentist may, with the instruments which are available to him cut the bar or grind the end of the bar so that it is the exact length he desires and so that it will match the shaping which he has formed in the lingual surfaces of the anterior teeth or in the central fossae of the molars. A single, double or triple bar may extend from the lingual surface of one tooth on one side of the bridge to the fossa of another tooth on the other side of the bridge (see FIGS. 29 and 30).

The invention lends itself to simplified operation by the dentist and to mass production techniques for the teeth and bars.

The procedure may be even more fully simplified as shown by the following summary.

ONE VISIT BONDED BRIDGE

I. Plastic Teeth

A. Dental Procedure
1. Upper and lower full impressions.
2. Bite registration (silicone bite registration material) or any bite registration material.
3. Shade and selection of appropriate teeth (plastic or any other material).

B. Laboratory Procedure
1. Mount casts on articulator using bite registration as a guide.
2. Plastic teeth selected to fill entire space (edentulous area) and to make occlusal contact with opposing jaw.
3. Teeth ground into corresponding ridge area and to the occlusion in centric and eccentric excursions.
4. Wax teeth in position to obtain accurate ridge lap and occlusal relationship and restoration of dental anatomy.
5. Accurately reproduce cast with the waxed-up teeth in position (matrix index).
6. This can produce a stone cast of the ground-in plastic teeth in stone which has mesio-distal and occlusal relationships.
7. Spray stone work model with silicone lubricant release agent.
8. Make accurate vacuum formed "index-matrix" of a heavy "clear" copolymer resin of high molecular weight (D. P. Vanguard material or any other appropriate material). Its unique properties allow it to remain permanently flexible yet strong and tough enough not only to hold the aligned teeth in position but also to permit light to pass through such as the ultraviolet light or halogen light. Set this index-matrix aside to be used later for the final tooth alignment and bonding of the "One visit bridge".
9. Form a horizontal channel mesio-distally in the middle third of the lingual surface of the ground in plastic teeth as a receptacle for the bar member.
10. Fit internal metal bar member or frame so that it is submerged in the prepared channel previously formed and extending onto the abutment teeth to a distance of $\frac{3}{4}$ of their mesio-distal occlusal width (see tooth 175 of FIG. 29).

Note: The anterior abutment teeth have each had a horizontal step or rest formed at the middle third of the lingual surface at a right angle to the long axis of the abutment teeth. In the case of a posterior tooth, deepen the central fossa mesio-distally to a distance of $\frac{3}{4}$ of its occlusal surface to a depth to submerge the metal bar member extension. Undercut the central fossa channel slightly and form a cavo-surface bevel. The stainless steel metal bar member varies from a gauge of 0.030–0.060 of an inch depending upon the stress factors present.

11. Using the matrix-index previously set aside, bond the plastic teeth together using methyl methacrylate and the proper shade self-curing acrylic, or any other suitable material.
12. Then carefully finish and polish the teeth with the metal bar member embedded therein.

This simple laboratory procedure may be performed by the dentist.

CLINICAL FABRICATION OF THE ONE VISIT COMPOSITE BRIDGE

Follow the steps set forth under the heading "ONE VISIT BONDED BRIDGE" A. 1–3, and B. 1–9, then:

(a) Using index matrix, fill appropriate teeth with correct shade of composite; seat back on original stone model, first removing waxed teeth;

(b) Holding matrix firmly, bond composite teeth using ultraviolet light 30 seconds on labial, lingual, incisal and occlusal areas of each tooth area; if halogen light is used, each exposure should be 20 seconds;

(c) Peel teeth out of matrix and repeat ultraviolet or halogen light procedure, then finish and polish, and set prosthesis aside together with index matrix to be used to bond to abutment teeth;

(d) Form a horizontal step or rest on the anterior teeth at the middle third of the lingual surface at right angles to the long axis of the abutment teeth. In case of a posterior tooth, deepen the central fossa mesio-distally to a distance of $\frac{3}{4}$ of the occlusal surface of the dento-enamel junction; undercut the central fossa (channel) slightly and form a cavo-surface bevel;

(e) Using the matrix index previously set aside seat composite bonded teeth in matrix and bond the artificial teeth to the abutment teeth. Make sure the abutment and artificial teeth are properly cleansed and etched;

(f) Etch lingual step and occlusal channel;

(g) Fill lingual steps and channel formed in fossa with the proper shade of composite filling material;

(h) Place matrix with contained teeth in position in mouth and hold firmly and accurately in position;

(i) Direct ultraviolet or halogen light to junction areas and abutment teeth for 30 seconds (20 seconds with halogen light) to the lingual, buccal, occlusal and incisal areas;

(j) Check articulation and make any slight adjustment of bite;

(k) Recall patient in week, glaze and dismiss.

II. Porcelain Teeth

A. Laboratory Preparation
1. Steps 1–9 are the same as for a plastic tooth replacement.
2. When porcelain teeth are used bond a metal frame to the porcelain made of Jelenko White gold-Olympia.
3. To obtain an accurate fit, wax up ground-in porcelain teeth and cast the metal frame making sure to use one index matrix as a guide to seat the teeth accurately on cast.
4. Fuse the metal bar member to the porcelain teeth.
5. Ridge lap accuracy is obtained by adapting platinum foil 0.001" to the ridge.
6. Place porcelain teeth in the matrix, add porcelain to the teeth seated in the index matrix and placed on the cast to obtain accurate ridge adaption; fire after removing carefully from matrix.
7. The laboratory preparation is now complete when the index matrix goes accurately to place with the teeth in position on the model.

III. Composite Teeth

1. Follow above steps 1 to 7.
2. Make the composite teeth by packing composite filling material or any other composite with the desired shade into the index matrix.

3. Polymerize with the ultraviolet or halogen light, which goes through the clear index matrix and hardens the composite teeth.

4. Follow steps B.8-B.10 above.

5. Laboratory preparation is now complete for composite teeth.

Reference is made to FIGS. 43 and 44. FIG. 43 shows an anterior tooth; the legends thereon indicate the various portions thereof. It is noted that the gingival margin of the crown does not encroach on the crevicular space or sulcus; it may be therefore referred to as supracrevicular. The crevicular space or sulcus refers to the space between the tooth surface on one side and the free margin of the gingival tissue or gum on the other side. FIG. 44 and the legends thereon show the utilization of a crown where a portion of the tooth has been fractured and again shows in particular the arrangement of the crown on the tooth so that the feather edge of the crown or the gingival margin thereof is supracrevicular.

A procedure for preparing a crown under such circumstances and particularly for use in connection with a tooth which might have been fractured is described below.

TECHNIQUE FOR RESTORING A BONDED ANTERIOR OR POSTERIOR CLINICAL CROWN

Rationale for Procedure:

I. Bonding:

(A) Chemical bond to enamel;

(B) Mechanical bond to dentin (undercuts and retentive grooves) to lock in composite (circumferential undercuts);

(C) Tooth preparation "gingival margin" must fall "superior" to "crevicular space" (location of gingival margin):

1. Prevents lacerating gingival tissue;
2. Prevents thermal and chemical sensitivity;
3. Prevents periodontitis (pyorrhea): non-encroachment or crevicular space or sulcus;
4. Prevents recurrent decay; there is a natural food scouring action when there is no encroachment on the crevicular space;
5. Prevents pulp exposure and devitalization;
6. There is no mutilation of the tooth.

II. Restoring a full crown on a vital tooth (due to attrition or fracture)

(A) Impression of full upper and lower jaw, including detail of fractured tooth area, and wax bite and shade;

(B) Articulate;

(C) Wax-up fractured teeth with inlay wax on cast, being careful to obtain proper occlusal relationship and mesio-distal contact-gingival margin is placed superior to crevicular space;

(D) Take impression of waxed up stone cast and pour another stone cast to be used for index matrix;

(E) Make a "clear" plastic copolymer vacuum formed "index matrix", set aside for final bonding.

III. Tooth Preparation for Bonding in Mouth:

(A) When there is sufficient enamel—use phosphoric acid 35 percent to etch for chemical bond;

(B) When insufficient enamel, i.e. where fracture has destroyed for example three-fourths of the tooth, but nerve has not been exposed, cement a metal thimble, well known per se, which will protect the nerve and also provide mechanical retention for the composite bonding.

IV. Actual Tooth Preparation Providing There is No Paupal Involvement:

(A) Tooth undercuts are not removed;

(B) Make circumferential gingival retention grooves;

(C) Make gingival margin superior to gingival crevice for feather edge finishing; no shoulder necessary.

V. Actual Tooth Bonding: (which may be done with any composite):

(A) Isolate tooth with rubber dam or (B) Cotton rolls and dri angles;

(C) Clean tooth thoroughly with engine bristle brush and flour of pumice or zircate;

(D) Wash tooth with clear water so as to remove all contaminants;

(E) Dry tooth thoroughly with air free of both oil mist and of water prevent salivary contamination throughout procedure;

(F) Retraction cord should be used to prevent gingival seepage and oozing;

(G) Keeping tooth absolutely dry, cover pulpal dentin with Pulpdent, Dycal and carboxylate cement;

(H) Keeping tooth absolutely dry, apply three coats of seal, over Dycal, Pulpdent and carboxylate cement.

Caution:

1. Prevent bridging;
2. Prevent crevical space encroachment of seal; remove any gingival irritation factors with dry brush applicator or explorer before polymerization;

(I) Polymerize with light (ultraviolet or halogen light) for 30 seconds (with ultraviolet light; 20 seconds with halogen light) each on all surfaces;

(J) Fill appropriate tooth in matrix index with selected shade of composite filling material. Seat matrix index carefully and accurately and hold in position while polymerizing 30 seconds (with ultraviolet light; 20 seconds with halogen light) each on all surface areas—the clear index matrix permits the ultraviolet or halogen light to penetrate and polymerize the composite;

(K) Remove matrix, still keeping tooth dry and free of salivary contamination and repeat 30 seconds (with ultraviolet light; 20 seconds with halogen light) polymerization as above;

(L) Finishing:

1. Gross contouring of flashing, or excessive composite, is removed with high speed diamond burs or ultrasonically after polymerization; fine finishing is done with composite fluted finishing burs by Midwest American. For the labial surface an interproximal finishing #7901 F.G. for lingual surface or #7408 F.G. It is best to use finishing burs dry. The above procedure is now followed by discs, for example the 3M Soflux brand finishing and polishing discs.
2. Glaze layer using seal and polymerization with ultraviolet light for 30 seconds each surface or with halogen light for 20 seconds on each surface;
3. Before dismissing patient, use damp gauze to remove any uncured material from surface of the hardened sealant to prevent the possibility of sensitization.

Figure 47:
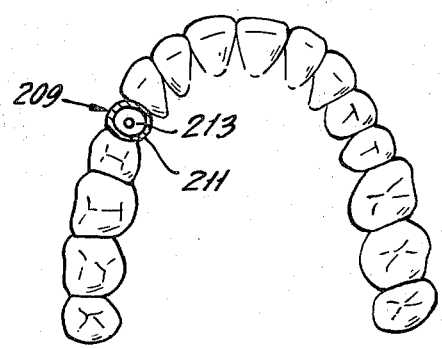
FIG. 47 is a view corresponding to FIG. 46, showing a conventional ceramco prosthesis emplaced in the mouth and showing one of the crowns of the prosthesis broken.
Figure 46:
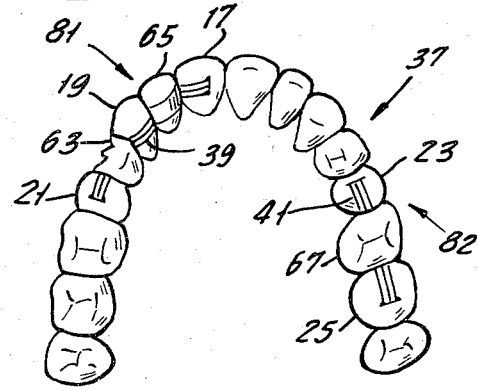
FIG. 46 is a view corresponding to FIG. 16, showing the prosthesis in place and showing one of the artificial teeth chipped.

FIGS. 46 and 47 illustrate two additional circumstances in which the procedure set forth herein can be advantageously applied. FIG. 46 shows a mouth in which two prostheses according to the present invention have been inserted and in which one of the prostheses has been damaged due to the chipping or fracture of one of the artificial teeth 63. FIG. 47 shows a mouth in which a conventional ceramco bridge has been inserted and in which a tooth 209 of bridge the crown 209 has been broken off, revealing the cross-section of the shell 211 of the tooth 209, as well as the artificial tooth stem 213. The chipped or fractured artificial tooth 63 of FIG. 46 and the fractured tooth 209 of FIG. 47 can both be quickly and efficiently repaired in the following manner according to the present invention.

I. Restoring a Chipped Artificial Tooth on a Conventional Ceramco Prosthesis or on a Prosthesis According to the Present Invention (A) Impression of full upper and lower jaw, including detail of fractured tooth area, and wax bite and shade.

(B) Articulate.

(C) Wax up fractured tooth or teeth with inlay wax on cast, being careful to obtain proper occlusal relationship and mesio-distal contact; gingival margin is placed superior to crevicular space.

(D) Take impression of waxed-up stone cast and pour another stone cast to be used for index matrix.

(E) Make a "clear" plastic copolymer vacuum-formed index matrix and set aside for final bonding.

II. Actual Tooth Repair (which may be done with any composite)

(A) Isolate tooth with rubber dam or with cotton rolls and dri angles.

(B) Clean tooth or teeth thoroughly with engine bristle brush and flour of pumice or zircate.

(C) Wash tooth or teeth with clear water so as to remove all contaminants.

(D) Dry tooth or teeth thorough with air free both of oil mist and of water and prevent salivary contamination throughout procedure.

(E) Retraction cord should be used to prevent gingival seepage and oozing.

(F) Fill appropriate tooth in matrix index with selected shade of composite to the extent necessary to replace the chipped off portion of the artificial tooth; seat matrix index carefully and accurately and hold in position while polymerizing all surface areas, each area being polymerized for about 20 seconds if using halogen light or for about 30 seconds if using ultraviolet light; the clear index matrix permits the ultraviolet or halogen light to penetrate and polymerize the composites.

(G) Remove matrix, still keeping tooth dry and free of salivary contamination and repeat polymerization for an additional 20 seconds (for halogen light) or 30 seconds (for ultraviolet light) for each surface area.

(H) Finishing:
1. Gross contouring of flashing, or excessive composite, is removed with high-speed diamond burs or ultrasonically after polymerization; fine finishing is done with composite fluted finishing burs by Midwest American; for the labial surface and interproximal finishing #7901 F.G. is preferred, and for lingual surface #7408 F.G. It is best to use finishing burs dry. The above procedure is now followed by discs, for example the 3M Sof-lux brand finishing and polishing discs.
2. Glaze layer using composite sealant and polymerize with ultraviolet light for 30 seconds or halogen light for 20 seconds on each surface.
3. Before dismissing patient, use damp gauze to remove any uncured material from surface of the hardened sealant to prevent the possibility of sensitization.

In the foregoing, there have been described various procedures and methods, all of which are founded on the concept that the dentist will do all or most of the operation of preparing, fitting, installing and making a bridge or crown and if possible, the operation be done on a one-visit basis. The process lends itself to the one-visit type of operation.

Most importantly, the invention necessarily entails the utilization of separate elements which may be stocked as previously pointed out and thereby lends itself to mass production, at least in part, of the bridge and the economies which result from mass production. Teeth of various sizes and shapes within reasonable limits of variations may be stocked. Support bars or struts may also be stocked and the dentist may be supplied with these materials as required by him, so that he may assemble the bridge, interconnect the elements of the bridge and actually mount the bridge in place in his office without being necessarily required to go outside to a dental laboratory or denturist. Where a porcelain tooth is to be used as part of a bridge and entailing the utilization of a kiln or other device for firing, the usual dental office may require the utilization of an outside dental laboratory, although if a dentist has such kiln in his office, then every element of the formation of the bridge may be performed by the dentist himself. In case a tooth on the prosthesis (bridge) should break, it can easily be restored in the mouth in one visit for nominal cost.

From the foregoing, those skilled in the art will now appreciate the numerous advantages of the present invention. In addition to those just described, it will also be understood that the index matrix simultaneously and automatically performs the three functions of: holding the prosthesis in place while the composite boding material is polymerized, ensuring that the prosthesis is so inserted that proper articulation is guaranteed, and shaping the composite bonding material, thereby saving the dentist the trouble of doing so and guaranteeing an aesthetically pleasing appearance.

In addition, if the artificial teeth of the prosthesis of the present invention (in the case of composite teeth) wear due to very hard use, emotional stress or the like, they can be restored to their proper form in the manner described above, instead of the prosthesis having to be removed from the mouth and rebuilt or replaced altogether and then reinserted.

In the foregoing, the present invention has been described in connection with preferred illustrative embodiments thereof. Since many variations and modifications will now be obvious to those skilled in the art, it is preferred that the scope of this invention be determined, not by the specific disclosures contained herein, but only by the appended claims.

What is claimed is:

1. A kit for making and inserting a dental bridge in a gap between natural teeth in a human mouth, said kit comprising:
a generally arch-shaped piece of a rigid material having approximately the shape of a geometric curve defined by the central fossae of the posterior teeth and the lingual surfaces of the anterior teeth of one jaw of a human mouth; said piece being adapted to have at least one artificial tooth mounted thereon and having such a cross-sectional shape that a length of said piece can be secured to at least one natural tooth to each side of said gap by means of being received in a groove formed in the surface of each of said natural teeth, and a sufficient quantity of copolymer usable for forming an ultraviolet light transmissive matrix for aligning said at least one artificial tooth.

2. The kit of claim 1 further comprising a plurality of said generally arch-shaped pieces, including at least one said piece having a hollow triangular cross-sectional shape having one open side.

3. The kit of claim 1, further comprising at least one said piece having a cross-sectional shape which is generally that of two parallel cylinders abutting each other.

4. The kit of claim 1 comprising a plurality of such generally arch-shaped pieces, including such pieces of each of at least three different sizes.

5. The kit of claim 1 comprising a plurality of such generally arch-shaped pieces, including at least one said piece having a shape defined by the teeth of an upper human jaw and including at least one such piece having a shape defined by the teeth of a lower human jaw.

6. The kit of claim 1, further comprising means for forming a bond between an artificial tooth and a length of said generally arch-shaped piece for permanently mounting the artificial tooth thereon.

7. The kit of claim 6, wherein said means for forming a bond comprises a substance which forms a bond upon being photocured by exposure to ultraviolet light, and wherein said kit further comprises a lamp for producing ultraviolet light.

8. The kit of claim 7, wherein said lamp is a halogen lamp.

9. The kit of claim 1, further comprising a set of instructions explaining in detail the procedure to be followed in making and inserting said bridge.

10. The kit of claim 1, further comprising means for modifying the shape of a length of said piece to make it conform exactly to the mouth of a particular patient.

11. The kit of claim 1, further comprising a composite bonding material.

12. The kit of claim 1, wherein said generally arch-shaped piece comprises stainless steel.

13. The kit of claim 12, further comprising coating material for coating at least a portion of said generally arch-shaped piece to mask it.

14. The kit of claim 13, wherein said coating material includes coating material of a plurality of different shades, for coating said portion with a shade to match the shade of a particular patient's natural teeth.

15. The process of making and inserting a dental bridge between adjacent teeth, comprising the steps of:

arranging a sufficient number of artificial teeth on an arched contoured longitudinal support to fill the space between said adjacent teeth and securing said artificial teeth on said longitudinal support;

forming a step in the lingual surface of an anterior tooth adjacent to the area in which the bridge is inserted; the step being defined by a single surface extending in the buccal direction and a single surface extending in the inclusive direction with respect to the anterior tooth;

the depth of said step being such that the longitudinal support may be substantially submerged therein;

etching the formed step surface to release any interprismatic cement which is exposed after the step is formed;

bonding said longitudinal support extensions in said step; and contouring said lingual surface to a smooth regular surface substantially similar to the original surface prior to formation of said step.

16. The process of making and inserting a dental bridge between adjacent teeth, comprising the steps of:

arranging a sufficient number of artificial teeth on an arched contoured longitudinal support to fill the space between said natural teeth and bonding said artificial teeth on said longitudinal support;

forming the central fossa of a posterior tooth adjacent to the abutment teeth into a channel in which the bridge is inserted, the channel being of a depth which will receive and submerge said support;

etching said channel to release any interprismatic cement exposed after the channel is formed;

undercutting said channel where the deepened fossa passes through the posterior tooth at a position in the posterior tooth that is removed from the nerve thereof;

placing one end of said longitudinal support in said channel and bonding the same therein.

17. The process of claim 15 or 16, wherein the space between the adjacent teeth requires a plurality of artificial teeth; and a plurality of artificial teeth are assembled on each longitudinal support.

18. The process of claim 15, wherein the adjacent teeth on each side of said space comprise anterior teeth; said longitudinal support being inserted to extend from a step in the lingual surface of one anterior natural tooth to a step in the lingual surface of the anterior tooth on the opposite side of said space.

19. The process of claim 16, wherein the natural teeth on each side of the space are posterior teeth;

said longitudinal support being inserted to extend from the channeled fossa of one tooth to the channeled fossa of the tooth on the opposite side.

20. The process of claim 17, wherein the tooth on one side of the space is an anterior tooth and the tooth on the other side is a posterior tooth, the longitudinal support being inserted to extend from the lingual surface of the anterior tooth to the channel in the fossa of the posterior tooth.

21. The process of claim 17, wherein the adjacent teeth on each side of the space comprise both an anterior tooth and a posterior tooth;

said longitudinal support being inserted to extend both into the step in said anterior tooth and the channel in the fossa of the posterior tooth.

22. The process of claim 18, wherein said longitudinal support is extended to an adjacent bicuspid.

23. The process of claim 19, wherein said longitudinal support extends to an adjacent bicuspid.

24. The process of making and inserting a dental bridge between adjacent teeth, comprising the steps of:

arranging a sufficient number of artificial teeth on an arched contoured longitudinal support to fill the space between said adjacent teeth and securing said artificial teeth on said longitudinal support:

forming an ultraviolet light transmissive matrix having first portions corresponding to the natural tooth anatomy and second portions corresponding to the arranged artificial teeth, said first and second portions being aligned with respect to one another;

forming a step in the lingual surface of an anterior tooth adjacent to the area in which the bridge is inserted; the step being defined by a single surface extending in the buccal direction and a single surface extending in the inclusive direction with respect to the anterior tooth;

the depth of said step being such that the longitudinal support may be substantially submerged therein;

etching the formed step surface to release any interprismatic cement which is exposed after the step is formed:

applying bonding material which cures upon being exposed to ultraviolet light to said step;

aligning said artificial teeth with said adjacent teeth using said matrix by placing said matrix over said artificial and adjacent teeth so that an end of said longitudinal support is disposed in said step; and exposing said matrix to ultraviolet light, whereby said bonding material is cured by ultraviolet light passing through said matrix and said longitudinal support bonded in said step.

25. The process of making and inserting a dental bridge between adjacent teeth, comprising the steps of:

arranging a sufficient number of artificial teeth on an arched contoured longitudinal support to fill the space between said adjacent teeth and securing said artificial teeth on said longitudinal support;

forming an ultraviolet light transmissive matrix having first portions corresponding to the natural tooth anatomy and second portions corresponding to the arranged artificial teeth, said first and second portions being aligned with respect to one another;

forming a step in the lingual surface of an anterior tooth adjacent to the area in which the bridge is inserted; the depth of said step being such that the longitudinal support may be submerged therein;

etching the formed step surface to release any interprismatic cement exposed after the step is formed;

applying a boding material to said etched step which cures upon being exposed to ultraviolet light;

aligning said artificial teeth with said adjacent teeth using said matrix by placing said matrix over said artificial and adjacent teeth; and bonding said longitudinal support extensions in said step by exposing said matrix to ultraviolet light, whereby said bonding material is cured by ultraviolet light transmitted through said matrix.

26. The process of claims 15, 24 or 25 further comprising:

limiting the depth of said step consistent with the submergence of the thickness of said longitudinal support therein to the depth of the enamel to the extent that the thickness of the enamel permits.

27. The process of claims 15, 16, 24 or 25 further comprising the steps of:

(a) applying a first layer of calcium hydroxide to the etched step formed in the tooth;

(b) applying a second layer of calcium hydroxide containing a hardening agent over the first calcium hydroxide layer, (c) applying a layer of carboxylate cement over the second calcium hydroxide layer, and (d) applying a composite seal over the carboxylate cement, all of steps (a), (b), (c) and (d) being performed before placing the bridge in position in the mouth.

28. The process of claim 27 further comprising the step of curing the applied composite seal before placing the bridge in position in the mouth.

29. The process of claim 27 further comprising the step of curing the applied composite seal while the composite bonding material is cured.

* * * * *